US010383928B2

(12) United States Patent
Gaudernack et al.

(10) Patent No.: US 10,383,928 B2
(45) Date of Patent: Aug. 20, 2019

(54) TELOMERASE POLYPEPTIDE VACCINE FOR TREATING CANCER

(71) Applicant: ULTIMOVACS AS, Oslo (NO)

(72) Inventors: Gustav Gaudernack, Oslo (NO); Anne-Marie Rasmussen, Oslo (NO); Else Marit Inderberg Suso, Oslo (NO)

(73) Assignee: ULTIMOVACS AS, Oslo (NO)

( * ) Notice: Subject to any disclaimer, the term of this patent is extended or adjusted under 35 U.S.C. 154(b) by 0 days.

(21) Appl. No.: 15/498,733

(22) Filed: Apr. 27, 2017

(65) Prior Publication Data
US 2017/0232088 A1 Aug. 17, 2017

Related U.S. Application Data

(62) Division of application No. 13/578,969, filed as application No. PCT/EP2011/000980 on Feb. 15, 2011, now Pat. No. 9,657,068.

(30) Foreign Application Priority Data

Feb. 16, 2010 (EP) .................................. 10250265

(51) Int. Cl.
*C07K 7/06* (2006.01)
*C07K 7/08* (2006.01)
*C12N 9/12* (2006.01)
*A61K 38/00* (2006.01)
*A61K 39/00* (2006.01)
*C07K 14/435* (2006.01)

(52) U.S. Cl.
CPC ............ *A61K 39/0011* (2013.01); *C07K 7/06* (2013.01); *C07K 7/08* (2013.01); *C07K 14/435* (2013.01); *C12N 9/1276* (2013.01); *C12Y 207/07049* (2013.01); *A61K 38/00* (2013.01); *A61K 2039/5154* (2013.01); *A61K 2039/53* (2013.01)

(58) Field of Classification Search
None
See application file for complete search history.

(56) References Cited

U.S. PATENT DOCUMENTS

| | | |
|---|---|---|
| 5,595,756 A | 1/1997 | Bally et al. |
| 5,919,656 A | 7/1999 | Harrington et al. |
| 5,981,707 A | 11/1999 | Harrington et al. |
| 6,174,703 B1 | 1/2001 | Harrington et al. |
| 6,337,200 B1 | 1/2002 | Morin |
| 6,440,735 B1 | 8/2002 | Gaeta |
| 6,608,188 B1 | 8/2003 | Tsuchiya et al. |
| 6,610,839 B1 | 8/2003 | Morin et al. |
| 6,767,719 B1 | 7/2004 | Morin et al. |
| 6,916,642 B1 | 7/2005 | Kilian et al. |
| 7,091,021 B2 | 8/2006 | Morin |
| 7,199,234 B2 | 4/2007 | Morin et al. |
| 7,262,288 B1 | 8/2007 | Cech et al. |
| 7,297,488 B2 | 11/2007 | Cech et al. |
| 7,390,891 B1 | 6/2008 | Harrington et al. |
| 7,402,307 B2 | 7/2008 | Gaeta |
| 7,413,864 B2 | 8/2008 | Cech et al. |
| 7,517,971 B1 | 4/2009 | Cech et al. |
| 7,585,622 B1 | 9/2009 | Cech et al. |
| 7,622,549 B2 | 11/2009 | Cech et al. |
| 7,750,121 B2 | 7/2010 | Cech et al. |
| 7,776,539 B2 | 8/2010 | Holcomb et al. |
| 7,824,849 B2 | 11/2010 | Gaeta |
| 7,879,609 B2 | 2/2011 | Morin et al. |
| 7,939,251 B2 | 5/2011 | Holcomb et al. |
| 8,003,773 B2 | 8/2011 | Langlade-demoyen et al. |
| 8,168,769 B2 | 5/2012 | Weiner et al. |
| 8,222,392 B2 | 7/2012 | Cech et al. |
| 8,236,774 B2 | 8/2012 | Cech et al. |
| 8,252,282 B2 | 8/2012 | Santos |
| 8,362,209 B2 | 1/2013 | Santos |
| 8,697,084 B2 | 4/2014 | Weiner et al. |
| 8,709,995 B2 | 4/2014 | Cech et al. |
| 8,796,438 B2 | 8/2014 | Morin |
| 8,858,931 B2 | 10/2014 | Langlade-Demoyen et al. |
| 9,290,546 B2 | 3/2016 | Weiner et al. |
| 9,376,471 B2 | 6/2016 | Weiner et al. |

(Continued)

FOREIGN PATENT DOCUMENTS

| | | |
|---|---|---|
| EA | 199900349 A1 | 6/2000 |
| EP | 0841396 | 5/1998 |
| EP | 0939823 | 9/1999 |
| EP | 0954585 | 11/1999 |
| EP | 1045697 | 10/2000 |
| EP | 1068296 | 1/2001 |
| EP | 1126872 A1 | 8/2001 |
| EP | 1133552 | 9/2001 |
| EP | 1504090 | 2/2005 |
| EP | 1572090 | 9/2005 |
| EP | 1748067 | 1/2007 |
| EP | 1761640 | 3/2007 |
| EP | 1776141 | 4/2007 |

(Continued)

OTHER PUBLICATIONS

Borel et al (J Immunol Methods. Mar. 16, 1984;67(2):289-302).*

(Continued)

*Primary Examiner* — Brian Gangle
*Assistant Examiner* — Andrea K McCollum
(74) *Attorney, Agent, or Firm* — HoustonHogle LLP

(57) ABSTRACT

A polypeptide comprising the sequence of SEQ. ID NO. 2, 3, 4, 7 or 8. The polypeptide may have the sequence of an immunogenic fragment thereof comprising at least eight amino acids, wherein the immunogenic fragment is not one of SEQ. ID NOS. 6 or 11 to 16. The polypeptide may have a sequence having at least 80% sequence identity to the aforementioned polypeptide or immunogenic fragment. The polypeptide is less than 100 amino acids in length and does not comprise the sequence of any of SEQ. ID NOS. 10, 46, 56, 57 or 59 to 62 and does not consist of the sequence of SEQ ID NO. 58. The polypeptide is useful in the treatment or prophylaxis of cancer.

30 Claims, 11 Drawing Sheets

Specification includes a Sequence Listing.

(56) References Cited

U.S. PATENT DOCUMENTS

| | | | |
|---|---|---|---|
| 9,624,479 | B2 | 4/2017 | Langlade-Demoyen et al. |
| 9,657,068 | B2 | 5/2017 | Gaudernack et al. |
| 2002/0142457 | A1 | 10/2002 | Umezawa et al. |
| 2003/0143228 | A1 | 7/2003 | Chen et al. |
| 2003/0166270 | A1 | 9/2003 | Reddy et al. |
| 2003/0232409 | A1 | 12/2003 | Farris et al. |
| 2004/0106128 | A1 | 6/2004 | Majumdar et al. |
| 2005/0013825 | A1* | 1/2005 | Cech ............... C12N 9/1241 424/185.1 |
| 2006/0057129 | A1 | 3/2006 | Lebkowski et al. |
| 2006/0063255 | A1 | 3/2006 | Lebkowski et al. |
| 2006/0106196 | A1* | 5/2006 | Gaudernack ......... A61K 38/45 530/326 |
| 2007/0292448 | A1 | 12/2007 | Lebkowski et al. |
| 2008/0279871 | A1 | 11/2008 | Cech et al. |
| 2009/0142408 | A1 | 6/2009 | Lin et al. |
| 2009/0202499 | A1 | 8/2009 | Zanetti et al. |
| 2009/0304640 | A1 | 12/2009 | Diwan et al. |
| 2011/0053787 | A1 | 3/2011 | Brulliard et al. |
| 2011/0243910 | A1 | 10/2011 | Hahn et al. |
| 2011/0318380 | A1 | 12/2011 | Brix et al. |
| 2012/0149598 | A1 | 6/2012 | Inoue et al. |
| 2015/0087064 | A1 | 3/2015 | Morin |
| 2015/0250863 | A1 | 9/2015 | Cech et al. |
| 2016/0263203 | A1 | 9/2016 | Cech et al. |
| 2017/0232087 | A1 | 8/2017 | Gaudemack et al. |

FOREIGN PATENT DOCUMENTS

| | | |
|---|---|---|
| EP | 1910529 | 4/2008 |
| EP | 1994942 | 11/2008 |
| EP | 1783139 | 7/2009 |
| EP | 2080812 | 7/2009 |
| EP | 2213740 | 8/2010 |
| EP | 2242853 | 10/2010 |
| EP | 2258876 | 12/2010 |
| EP | 2337795 | 6/2011 |
| EP | 2402038 | 1/2012 |
| EP | 1333094 | 4/2012 |
| EP | 2049559 | 12/2012 |
| EP | 2578678 | 4/2013 |
| EP | 2110439 | 3/2014 |
| EP | 2708549 | 3/2014 |
| EP | 2594576 | 7/2015 |
| EP | 2626420 | 6/2016 |
| EP | 3037429 | 6/2016 |
| NO | 19983141 | 7/1998 |
| WO | 98/14593 A9 | 4/1998 |
| WO | WO 98/21343 | 5/1998 |
| WO | 0002581 A1 | 1/2000 |
| WO | 02094312 A1 | 11/2002 |
| WO | 03038047 A2 | 5/2003 |
| WO | 2010003520 A2 | 1/2010 |
| WO | 2010037395 A3 | 4/2010 |
| WO | 2011101173 A1 | 8/2011 |

OTHER PUBLICATIONS

Aloysius, M.M., et al., "Generation in vivo of Peptide-Specific Cytotoxic T Cells and Presence of Regulatory T Cells during Vaccination with hTERT (Class I and II) Peptide-Pulsed DCs," Journal of Translational Medicine, 7(18): 1-23 (Mar. 19, 2009). Twenty-three pages.
Beatty, G.L., et al., "Telomerase as a Universal Tumor Antigen for Cancer Vaccines," Expert Reviews of Vaccines, 7 (7): 881-887 (Sep. 2008). Seven pages.
Bernhardt, S.L., et al., "Telomerase peptide vaccination of patients with non-resectable pancreatic cancer: a dose escalating phase I/II study," British Journal of Cancer 95: 1474-1482 (2006). Nine pages.
Brunsvig, P.F., et al., "Telomerase Peptide Vaccination: A Phase I/II Study in Patients with Non-Small Cell Lung Cancer," Cancer Immunology Immunotherapy, 55(12): 1553-1564 (Feb. 2006). Twelve pages.
Brunsvig, P.F., et al., "Telomerase Peptide Vaccination in NSCLC: A Phase II Trial in Stage III Patients Vaccinated after Chemoradiotherapy and an 8-Year Update on a Phase I/II Trial," American Association for Cancer Research, 17(21):6847-6857 (Nov. 1, 2011). Twelve pages.
Counter, C.M., et al., "Telomerase activity is restored in human cells by ectopic expression of hTERT (hEST2), the catalytic subunit of telomerase," Oncogene 16:1217-1222 (1998). Six pages.
Delamarre, L., et al., "Differential Lysosomal Proteolysis in Antigen-Presenting Cells Determines Antigen Fate," Science 307:1630-1634 (Mar. 11, 2005). Five pages.
Genbank AB094676.1, "Felis catus mRNA for telomerase reverse transcriptase (TERT), partial cds," downloaded http://www.ncbi.nlm.nih.gov/nuccore/ab094676, Mar. 25, 2015. One page.
Genbank AB094677.1, "Canis familiaris mRNA for telomerase reverse transcriptase (TERT), partial cds," downloaded http://www.ncbi.nlm.nih.gov/nuccore/40316435?sat=34&satkey= . . . , Mar. 25, 2015. One page.
Goodell, V., et al., "Sensitivity and specificity of tritiated thymidine incorporation and ELISPOT assays in identifying antigen specific T cell immune responses," BMC Immunology 8(21):1-8 (Sep. 12, 2007). Eight pages.
Guy, C.S., et al., "Distinct TCR signaling pathways drive proliferation and cytokine production in T cells," Nature Immunology 14(3):262-272 (Mar. 2013). Eleven pages.
Harley, C.B., et al., "Telomerase, Cell Immortality, and Cancer," Cold Spring Harb Symp Quant Biol. LIX:307-315 (1994). 9 pages.
Hassan, C. et al., "The Human Leukocyte Antigen-presented Ligandome of B Lymphocytes," Molecular & Cellular Proteomics 12(7):1829-1843 (2013). Fifteen pages.
Hassan, C. et al., "Naturally Processed Non-canonical HLA-A*02:01 Presented Peptides," Journal of Biological Chemistry 290(5):2593-2603 (Jan. 30, 2015). Twelve pages.
Hoze, E., et al., "Predictor for the Effect of Amino Acid Composition on CD4+ T Cell Epitopes Preprocessing," J. Immunol Methods 391(0):163-173 (2013) with Exhibit B algorithm. Twenty-eight pages.
Hunger, R.E., et al., "Vaccination of patients with cutaneous melanoma with telomerase-specific peptides," Cancer Immunol Immunother 60:1553-1564 (2011). Twelve pages.
Inderberg-Suso, E-M, et al., "Widespread CD4+ T-cell reactivity to novel hTERT epitopes following vaccination of cancer patients with a single hTERT peptide GV1001," OncoImmunology 1:7:1-17 (2012) and supplementary materials. 24 pages.
International Preliminary Report on Patentability, dated Aug. 21, 2012, from International Application No. PCT/EP/2011/000980, filed on Feb. 15, 2011. Fourteen pages.
International Search Report, dated Aug. 6, 2011, from International Application No. PCT/EP/2011/000980, filed on Feb. 15, 2011. Eight pages.
Kim, N.W., et al., "Specific Association of Human Telomerase Activity with Immortal Cells and Cancer," Science 266:2011-2015 (1994). 5 pages.
Kondo, M.K., "The response of bovine beta-lactoglobulin-specific T-cell clones to single amino acid substitution of T-cell core epitope," Pediatr Allergy Immunol. 19:592-598 (2008). 7 pages.
Kyte, J.A., et al., "Telomerase peptide vaccination combined with temozolomide: A clinical ti\rial in stage IV melanoma patients," Clinical Cancer Research DOI:10.1158/1078-0432.CCR-11-0184 (2011). Thirty-nine pages.
Kyte, J.A., et al., "Unconventional Cytokine Profiles and Development of T Cell Memory in Long-Term Survivors After Cancer Vaccination," Cancer Immunology, Immunotherapy, 58(10): 1609-1626 (Feb. 2009). Eighteen pages.
Liu, J.P., et al., "Telomerase in Cancer Immunotherapy," BBA—Reviews on Cancer, 1805(1): 35-42 (Jan. 2010). Eight pages.
Malecek, K., et al., Engineering improved T cell receptors using an alanine-scan guided T cell display selection system,: Journal of Immunological Methods 392:1-11 (2013). 11 pages.
Melief, C.J.M, et al., "Immunotherapy of established (pre)malignant disease by synthetic long peptide vaccines," Nature Review/Cancer 8:351-360 (2008).

(56) References Cited

OTHER PUBLICATIONS

NCBI Blast Protein Sequence Comparison 2 Sequences (Apr. 12, 2014). Two pages.
Newbold, R.F., et al., "The significance of telomerase activation and cellular immortalization in human cancer," Mutagenesis 17:6:539-550 (2002). 12 pages.
Peruzzi, D. et al., "Telomerase and HER-2/neu as targets of genetic cancer vaccines in dogs," Vaccine 28:1201-1208 (2010). Eight pages.
Rodriguez, A., et al., "Selective transport of internalized antigens to the cytosol for MHC class I presentation in dendritic cells," Nature Cell Biology 1:362-368 (1999). Seven pages.
Rosalia, R.A., et al., "Dendritic cells process synthetic long peptides better than whole protein, improving antigen presentation and T-cell activation," Eur. J. Immunol. 43:2554-2565 (2013). Twelve pages.
Schroers, R., et al., "Identification of HLA DR7-Restricted Epitopes From Human Telomerase Reverse Transcriptase Recognized by CD4+ T-helper Cells," Cancer Research, 62(9): 2600-2605 (May 2002). Six pages.
Shay, J.W., et al., "Telomeres and telomerase in normal and cancer stem cells," FEGS Letters 584:3819-3825 (2010). Seven pages.
Shay, J.W. "Telomerase in Human Development and Cancer," Journal of Cellular Physiology 173:266-270 (1997). Five pages.
Su, Z., et al., "Telomerase mRNA-Transfected Dendritic Cells Stimulate Antigen-Specific CD8+ T Cell Responses in Patients With Metastatic Prostate Cancer," J. Immunol., 174(6): 3798-3807 (2004). Ten pages.
UniProt Q7YR69—Q7YR69_FELCA, "Telomerase reverse transcriptase (TERT)," last updated Sep. 30, 2003; downloaded http://www.uniprot.org/uniprot/Q7YR69, Apr. 16, 2015. Four pages.
UniProt Q76K45—Q76K45_CANFA, "Telomerase reverse transcriptase (TERT)," last updated Jul. 5, 2004; downloaded Oct. 24, 2014 from http://www.unipro.org/uniprot/Q76K45). Three pages.
Vermeij, R., "Potentiation of a p53-SLP vaccine by cyclophosphamide in ovarian cancer: a single-arm phase II study," International Journal of Cancer 131:E670-E680 (2012) Copyright 2011 UICC. Eleven pages.
Xie, M. et al., "A novel motif in telomerase reverse transcriptase regulates telomere repeat addition rate and processivity," Nucleic Acids Research 38(6):1982-1996 (Dec. 30, 2009). Fifteen pages.
Yazawa, M. et al., "Molecular Cloning of the Feline Telomerase Reverse Transcriptase (TERT) Gene and Its Expression in Cell Lines and Normal Tissues," J. Vet. Med. Sci. 65(5):573-577 (Jan. 17, 2003). Five pages.
Zeng G. et al., "Generation of NY-ESO-1 specific CD4+ and CD8+ T-Cells by a Single Peptide with Dual HMC Class I and Class II Specificities: A New Strategy for Vaccine Design," Cancer Research 62:3630-3635 (2002). Seven pages.
Zwaveling S. et al., Established Human Papillomavirus Type 16-Expressing Tumors Are Effectively Eradicated Following Vaccination with Long Peptides,: J Immunol 169:350-358 (2002). Ten pages.
2012139432/10, Decision of Grant by the Russian Patent Office with English translation, dated Nov. 2, 2015. Twenty-five pages including translation.
Bearss, D. et al., "Telomere Maintenance Mechanisms as a Target for Drug Development," Oncogene, vol. 19, pp. 6632-6641, 2000. Ten pages.
Hansen, G. et al., "Immunological Factors Influencing Clinical Outcome in Lung Cancer Patients after Telomerase Peptide Vaccination," Cancer Immunology and Immunotherapy, vol. 64, pp. 1609-1621, 2015. Thirteen pages.
Hu, Y. et al., "Long-term Outcomes of Helper Peptide Vaccination for Metastatic Melanoma," Annals of Surgery, vol. 262, No. 3, pp. 456-464, Sep. 2015. Nine pages.
Lee, D. et al., "Telomerase: A Potential Marker of Bladder Transitional Cell Carcinoma in Bladder Washes," Clinical Cancer Research, vol. 4, pp. 535-538, Mar. 1998. Four pages.
Mortier, M. et al., "Sequence Conservation Analysis and in silico Human Leukocyte Antigen-Peptide Binding Predictions for the Mtb72F and M72 Tuberculosis Candidate Vaccine Antigens," BioMed Central Immunology, vol. 16, No. 63. Fourteen pages.
Reed, C. et al., "Vaccination with Melanoma Helper Peptides Induces Antibody Responses Associated with Improved Overall Survival," Clinical Cancer Research, vol. 21, No. 17, pp. 3879-3887, Sep. 1, 2015. Nineteen pages.
Salazar, L. et al., "Immunization of Cancer Patients with HER-2/neu-Derived Peptides Demonstrating High-Affinity Binding to Multiple Class II Alleles," Clinical Cancer Research, vol. 9, pp. 5559-5565, Nov. 15, 2003. Eight pages.
Schmidt, J. et al., "In silico and Cell-Based Analyses Reveal Strong Divergence Between Prediction and Observation of T-Cell-Recognized Tumor Antigen T-Cell Epitopes," Journal of Biological Chemistry, vol. 292, No. 28, pp. 11840-11849, 2017. Eighteen pages.
Slingluff, Jr., C. et al., "Evaluation of the Sentinel Immunized Node for Immune Monitoring of Cancer Vaccines," Annals of Surgical Oncology, vol. 15, No. 12, Dec. 2008, pp. 3538-3549. Twenty pages.
Van Poelgeest, M. et al., "HPV16 Synthetic Long Peptide (HPV16-SLP) Vaccination Therapy of Patients with Advanced or Recurrent HPV16-Induced Gynecological Carcinoma, a Phase II trial," Journal of Translational Medicine, vol. 11, No. 88, 2013. Fourteen pages.
Yamshchikov, G. et al., "Evaluation of Peptide Vaccine Immunogenicity in Draining Lymph Nodes and Peripheral Blood of Melanoma Patients," International Journal of Cancer, vol. 92, pp. 703-711, 2001. Nine pages.
Co-pending U.S. Appl. No. 15/498,728, filed Apr. 27, 2017.
Abrahamsen, I.W., et al., "Targeting B cell leukemia with highly specific allogeneic T cells with a public recognition motif," Leukemia 24:1901-1909 (2010). Nine pages.
EP 11707345.2 Office Action dated Mar. 22, 2016 in related case. Ten pages.
Aagaard, L. et al., "RNAi Therapeutics: Principles, Prospects and Challenges," Advanced Drug Delivery Reviews, vol. 59, pp. 75-86, 2007. Twelve pages.
Auerbach, R. et al., "Angiogenesis Assays: Problems and Pitfalls," Cancer and Metastasis Reviews, vol. 19, pp. 167-172, 2000. Six pages.
Bonovas, S. et al, "Cancer Chemoprevention: A Summary of the Current Evidence," Anticancer Research, vol. 28, pp. 1857-1866, 2008. Ten pages.
Bork, P., "Powers and Pitfalls in Sequence Analysis: The 70% Hurdle," Genome Research, vol. 10, pp. 398-400, 2000. Four pages.
Bowie, J.U. et al., "Deciphering the Message in Protein Sequences: Tolerance to Amino Acid Substitutions," Science, vol. 247, No. 4948, pp. 1306-1310, 1990. Six pages.
Burgess, W. et al., "Possible Dissociation of the Heparin-Binding and Mitogenic Activities of Heparin-Binding (Acidic Fibroblast) Growth Factor-1 from Its Receptor-Binding Activities by Site-Directed Mutagenesis of a Single Lysine Residue," Journal of Cell Biology, vol. 111, pp. 2129-2138, 1990. Ten pages.
Gura, T., "Systems for Identifying New Drugs Are Often Faulty," Science, vol. 278, pp. 1041-1042, 1997. Two pages.
Jain, R.K., "Barriers to Drug Delivery in Solid Tumors," Scientific American, pp. 58-65, 1994. Eight pages.
Lazar, E. et al., "Transforming Growth Factor α: Mutation of Aspartic Acid 47 and Leucine 48 Results in Different Biological Activities," Molecular and Cellular Biology, vol. 8, No. 3, pp. 1247-1252, 1988. Six pages.
McKeague, M. et al., "Challenges and Opportunities for Small Molecule Aptamer Development," Journal of Nucleic Acids, 2012. Twenty pages.
Sporn, M. et al., "Chemoprevention of Cancer," Carcinogenesis, vol. 21, No. 3, pp. 525-530, 2000. Six pages.
Warzocha, K. et al., "Antisense Strategy: Biological Utility and Prospects in the Treatment of Hematological Malignancies," Leukemia and Lymphoma, vol. 24, pp. 267-281, 1997. Fifteen pages.
Aamdal E., et al., "Telomerase peptide vaccine combined with ipilimumab in metastatic melanoma: Reports from a phase I trial," Abstract, Annals of Oncology, 28(5):410 (2017). One page.

(56) References Cited

OTHER PUBLICATIONS

FDA News Release, "FDA approves first cancer treatment for any solid tumor with a specific genetic feature," May 23, 2017. <https://www.fda.gov/newsevents/newsroom/pressannouncements/ucm560167.htm>. Three pages.

Guren, T.K., et al. (Brunsvig), "Telomerase peptide vaccine treatment of patients with locally advanced or metastatic non-small cell lung cancer: Report from a phase I/IIA trial," Journal for ImmunoTherapy of Cancer, 5(Suppl 2):86; pp. 67-68 (2017). Two pages.

Kailashiya, C., et al., "Telomerase based anticancer immunotherapy and vaccines approaches," Vaccine, 35:5768-5775 (2017). Eight pages.

Lilleby, W., et al., "Phase I/IIa clinical trial of a novel hTERT peptide vaccine in men with metastatic hormone-naive prostate cancer," Cancer Immunol Immunother, DOI 10.1007/s00262-017-1994-y. Springer-Verlag Berlin Heidelberg (2017) Eleven pages.

Nielsen, M., et al., "MHC Class II epitope predictive algorithms," Immunology, 130:319-328 (2010). Ten pages.

HLA-DRB1 alleles, sorted by allele frequency (2008) <http://pypop.org/popdata/2008/byfreq-DRB1.php.html>.

Bernhardt, S.L. et al., "Imiquimod a new adjuvant for telomerase peptide vaccine: A phase I trial in patients with inoperable pancreatic cancer," Abstract, Journal of Clinical Oncology, 23 (16 Suppl):9623-9623. (Jun. 1, 2005). 5 pages.

Brunsvig, P.F. et al., "A phase I/II study of telomerase peptide vaccination of patients with non-small cell lung cancer," Abstract, Journal of Clinical Oncology, 23(16 Suppl):2580-2580 (Jun. 1, 2005). 5 pages.

Singh, H. et al., "ProPred: prediction of HLA-DR binding sites," Abstract, Bioinformatics, 17 (12):1236-1237 (Dec. 2001). 3 pages.

International Application No. PCT/US97/21248 filed Nov. 13, 1997, published as WO 98/21343 on May 22, 1998, which claims priority to U.S. Appl. No. 08/871,189 filed Nov. 15, 1996; 08/873,039 filed Jun. 11, 1997; and 08/951,733 filed Oct. 16, 1997.

* cited by examiner

TELOMERASE POLYPEPTIDE VACCINE FOR TREATING CANCER

RELATED APPLICATIONS

This application is a Division of U.S. application Ser. No. 13/578,969, which is a § 371 National Phase Application of International Application No. PCT/EP2011/000980, filed on Feb. 15, 2011, which claims priority to European Application No. 10250265.5, filed on Feb. 16, 2010, all of which are incorporated herein by reference in their entirety.

INCORPORATION BY REFERENCE OF MATERIAL IN ASCII TEXT FILE

This application incorporates by reference the Sequence Listing contained in the following ASCII text file:
File name: 0332-0001US3_PN791345USB_Sequence_Listing.TXT; created Apr. 12, 2017, 11 KB in size.

FIELD OF THE INVENTION

The present invention relates to a polypeptide and to a nucleic acid molecule consisting of a nucleotide sequence encoding the polypeptides. The invention also relates to a cocktail of polypeptides and to a cocktail of nucleic acid molecules. The invention further relates to a pharmaceutical composition comprising such a polypeptide, nucleic acid molecule or cocktail thereof. In addition, the present invention relates to methods of treatment or prophylaxis of cancer in a patient comprising administering the polypeptide, nucleic acid molecule or cocktail to the patient.

BACKGROUND OF THE INVENTION

Cancer is a disease characterised by new and abnormal growth of cells within an individual. Cancer develops through a multi-step process involving several mutational events that allow cancer cells to develop, that is to say cells which display the properties of invasion and metastasis. Generally speaking, there are two classes of genes in which mutation can occur and give rise to cancer: oncogenes and tumour suppressor genes. The activation of oncogenes gives rise to new properties of the cell such as hyperactive growth and division, protection against programmed cell death, loss of respect for normal tissue boundaries and the ability to become established in diverse tissue environments. Tumour suppressor genes can be inactivated which permits the loss of normal functions in the cell such as accurate DNA replication, control over the cell cycle, orientation, and adhesion within tissues and interaction with protective cells of the immune system.

Numerous approaches have been proposed for the treatment and prophylaxis of cancer. One approach is the use of antigenic peptides which comprise fragments of tumour specific antigens. Such antigenic peptides, when administered to an individual, elicit an MHC class I or class II restricted T-cell response against cells expressing the tumour specific antigens.

It is to be appreciated that in order for such a T-cell response to occur, the antigenic polypeptide must be presented on an MHC molecule. There is a wide range of variability in MHC molecules in human populations. In particular, different individuals have different HLA alleles which have varying binding affinity for polypeptides, depending on the amino acid sequence of the polypeptides. Thus an individual who has one particular HLA allele may have MHC molecules that will bind a polypeptide of a particular sequence whereas other individuals lacking the HLA allele will have MHC molecules unable to bind and present the polypeptide (or, at least, their MHC molecules will have a very low affinity for the polypeptide and so present it at a relatively low level).

It has also been proposed to provide a vaccine comprising a nucleic acid molecule that encodes such an antigenic peptide. Such a vaccine operates by way of a similar principle except that after administration of the vaccine to an individual in need of treatment, the nucleic acid molecule is transcribed (if it is DNA molecule) and translated in order to synthesise the peptide which is then bound and presented by an MHC molecule as described above.

Telomerase is an enzyme that has the function of replicating the 3' end of the telomerase regions of linear DNA strands in eukaryotic cells as these regions cannot be extended by the enzyme DNA polymerase in the normal way. The telomerase enzyme comprises a telomerase reverse transcriptase subunit ("TERT" or "hTERT" for humans) and telomerase RNA. By using the telomerase RNA as a template, the telomerase reverse transcriptase subunit adds a repeating sequence to the 3' end of chromosomes in eukaryotic cells in order to extend the 3' end of the DNA strand.

It has been observed that the telomerase enzyme is activated in the vast majority of all human tumours. It is believed that this occurs because, without the expression of the telomerase enzyme, the telomeres of cells are gradually lost, and the integrity of the chromosomes decline with each round of cell division of a cell which ultimately results in apoptosis of the cells. Thus, expression of the telomerase enzyme is generally necessary for a cancer cell to develop because without such expression, programmed cell death will usually occur by default. In view of the role of telomerase activation in cancer, telomerase has been regarded as a tumour specific antigen and thus as a potential target for cancer therapy.

WO03/038047 discloses a peptide designated as T672 which is reported to elicit a proliferative T-cell response from cells of healthy donors. Various other peptides of hTERT are also disclosed but were not subject to any experimental testing.

WO00/02581 discloses polypeptides of telomerase which elicit an MHC class I and/or class II restricted T-cell response. One of the polypeptides disclosed (having the amino acid sequence EARPALLTSRLRFIPK, which is also known as GV1001) is undergoing a phase III clinical trial (Telo Vac) in the UK in pancreatic cancer patients as a vaccine treatment.

WO02/094312 discloses certain polypeptides derived from hTERT.

Liu J P et al (2009 Telomerase in cancer immunotherapy Biochim Biophys Acta. September 12) reviewed 26 hTERT peptides that had been shown to induce efficient immune responses to hTERT positive tumour cells.

Dendritic cells transfected with hTERT mRNA have also previously been employed to treat metastatic prostate cancer patients (Su et al, 2005, Telomerase mRNA-transfected dendritic cells stimulate antigen-specific CD8+ and CD4+ T cell responses in patients with metastatic prostate cancer. *J Immunol.* 174(6):3798-807). Su et al demonstrated successful generation of hTERT-specific T cell responses measured as IFNγ secreting CD8+ T cells and CTL-mediated killing of hTERT targets. Four patients also experienced partial clinical responses. However, no hTERT epitopes were characterized in these studies.

There is always a need for further antigenic polypeptides (and nucleic acid molecules which encode such polypeptides) for the treatment of cancer, such as polypeptides which can elicit a more effective immune response in individuals and/or polypeptides which are presented by HLA alleles present in a greater proportion of the population.

The present seeks to alleviate one or more of the above problems.

SUMMARY OF THE INVENTION

According to a first aspect of the present invention, there is provided a polypeptide comprising a sequence selected from:
  i) SEQ. ID NOS. 2, 3, 4, 7, 8 or 9;
  ii) the sequence of an immunogenic fragment of i) comprising at least eight amino acids, wherein the immunogenic fragment is not one of SEQ. ID NOS. 6 or 11 to 16; or
  iii) a sequence having at least 80% sequence identity to i) or ii),
wherein the polypeptide is less than 100 amino acids in length and wherein the polypeptide does not comprise the sequence of either of SEQ. ID NOS. 10 or 56.

It is preferred that the polypeptide does not comprise the sequence of any of SEQ. ID NOS. 46, 57 or 59 to 62 and does not consist of the sequence of SEQ ID NO. 58.

The polypeptide is isolated which is to say that it does not form part of the protein (hTERT) in which it naturally occurs.

The polypeptide is capable of eliciting a T-cell response in a healthy patient with an HLA allele appropriate for displaying the polypeptide.

Conveniently, the sequence of the polypeptide according to the first aspect of the present invention is defined as a sequence selected from:
  i) SEQ. ID NO. 1;
  ii) the sequence of an immunogenic fragment of i) comprising at least eight amino acids, wherein the immunogenic fragment is not one of SEQ. ID NOS. 6, 11 to 16 or 56; and
  iii) a sequence having at least 80% sequence identity to i) or ii),
wherein the polypeptide is less than 100 amino acids in length. That is to say, the polypeptide may comprise the sequence of SEQ. ID NO. 1 which incorporates the sequences of SEQ. ID NOS. 2 and 3 and need not be in addition to the sequences of SEQ. ID NOS. 2 and 3.

It is preferred that the polypeptide does not consist of the sequence of SEQ ID NO. 58.

Preferably, the immunogenic fragment has the sequence of any one of SEQ. ID NOS. 17 to 40.

Advantageously, the polypeptide is less than or equal to 80, 50, 30, 20 or 11 amino acids in length.

According to a second aspect of the present invention, there is provided a nucleic acid molecule consisting of a nucleotide sequence encoding a polypeptide according to the invention.

The nucleic acid molecule is isolated which is to say that it does not form part of the gene (the telomerase gene) in which it naturally occurs.

According to a third aspect of the present invention, there is provided a cocktail of polypeptides comprising at least two different polypeptides comprising sequences selected from the group consisting of:
  i) SEQ. ID NOS. 2 to 7;
  ii) the sequence of an immunogenic fragment of i) comprising at least eight amino acids; and
  iii) a sequence having at least 80% sequence identity to i) or ii),
wherein each polypeptide is less than 100 amino acids in length. It is preferred that said at least two polypeptides are different in the sense that the sequence defined in i) is different for each polypeptide.

Conveniently, the sequence of at least one of the polypeptides is defined as comprising a sequence selected from the group consisting of:
  i) SEQ. ID NOS. 1, 7, 8, 9 or 10;
  ii) the sequence of an immunogenic fragment of i) comprising at least eight amino acids; and
  iii) a sequence having at least 80% sequence identity to i) or ii),
wherein the polypeptides are less than 100 amino acids in length. For example, one of the polypeptides may comprise the sequence of SEQ. ID NO. 1 which incorporates SEQ. ID NOS. 2 and 3 and need not be in addition to the sequence of SEQ. ID NOS. 2 and 3.

Advantageously, the at least two different polypeptides comprise a cocktail of polypeptides selected from the group consisting of:
  i) a cocktail of: a polypeptide comprising the sequence of SEQ. ID NO. 1 or a sequence having at least 80% sequence identity thereto or an immunogenic fragment thereof comprising at least eight amino acids; a polypeptide comprising the sequence of SEQ. ID NO. 7 or a sequence having at least 80% sequence identity thereto or an immunogenic fragment thereof comprising at least eight amino acids; and a polypeptide comprising the sequence of SEQ. ID NO. 9 or a sequence having at least 80% sequence identity thereto or an immunogenic fragment thereof comprising at least eight amino acids;
  ii) a cocktail of: a polypeptide comprising the sequence of SEQ. ID NO. 1 or a sequence having at least 80% sequence identity thereto or an immunogenic fragment thereof comprising at least eight amino acids; a polypeptide comprising the sequence of SEQ. ID NO. 8 or a sequence having at least 80% sequence identity thereto or an immunogenic fragment thereof comprising at least eight amino acids; and a polypeptide comprising the sequence of SEQ. ID NO. 9 or a sequence having at least 80% sequence identity thereto or an immunogenic fragment thereof comprising at least eight amino acids; and
  iii) a cocktail of: a polypeptide comprising the sequence of SEQ. ID NO. 1 or a sequence having at least 80% sequence identity thereto or an immunogenic fragment thereof comprising at least eight amino acids; a polypeptide comprising the sequence of SEQ. ID NO. 8 or a sequence having at least 80% sequence identity thereto or an immunogenic fragment thereof comprising at least eight amino acids; and a polypeptide comprising the sequence of SEQ. ID NO. 10 or a sequence having at least 80% sequence identity thereto or an immunogenic fragment thereof comprising at least eight amino acids,
  wherein each polypeptide is less than 100 amino acids in length.

Preferably, the or each immunogenic fragment has a sequence of any one of SEQ. ID NOS. 17 to 40.

According to a fourth aspect of the present invention, there is provided a cocktail of nucleic acid molecules comprising at least two different nucleic acid molecules consisting of a nucleic acid sequence encoding a polypeptide comprising a sequence selected from a group consisting of:
  i) SEQ. ID NOS. 2 to 7;
  ii) the sequence of an immunogenic fragment of i) comprising at least eight amino acids; and
  iii) a sequence having at least 80% sequence identity to i) or ii);
wherein the polypeptide is less than 100 amino acids in length. It is preferred that said at least two nucleic acid molecules are different in the sense that the sequence defined in i) is different for each nucleic acid molecule.

Advantageously, at least one nucleic acid molecule is defined as consisting of a nucleic acid sequence encoding a polypeptide comprising a sequence selected from a group consisting of:
  i) SEQ. ID NOS. 1, 7, 8, 9 or 10;
  ii) the sequence of an immunogenic fragment of i) comprising at least eight amino acids; and
  iii) a sequence having at least 80% sequence identity to i) or ii),
wherein the polypeptides are less than 100 amino acids in length. For example, a nucleic acid molecule may consist of the nucleic acid sequence encoding a polypeptide comprising SEQ. ID NO. 1 which incorporates SEQ. ID NOS. 2 and 3 and the polypeptide need not additionally comprise the sequence of SEQ. ID NOS. 2 and 3.

Preferably, the at least two different nucleic acid molecules comprise a cocktail of nucleic acid molecules selected from the group consisting of:
  i) a cocktail of: a nucleic acid molecule consisting of a nucleic acid sequence encoding a polypeptide comprising a primary sequence of SEQ. ID NO. 1 or a secondary sequence having at least 80% sequence identity to the primary sequence or an immunogenic fragment of the primary sequence or the secondary sequence comprising at least eight amino acids; a nucleic acid molecule consisting of a nucleic acid sequence encoding a polypeptide comprising a primary sequence of SEQ. ID NO. 7 or a secondary sequence having at least 80% sequence identity to the primary sequence or an immunogenic fragment of the primary sequence or the secondary sequence comprising at least eight amino acids; and a nucleic acid molecule consisting of a nucleic acid sequence encoding a polypeptide comprising a primary sequence of SEQ. ID NO. 9 or a secondary sequence having at least 80% sequence identity to the primary sequence or an immunogenic fragment of the primary sequence or the secondary sequence comprising at least eight amino acids;
  ii) a cocktail of: a nucleic acid molecule consisting of a nucleic acid sequence encoding a polypeptide comprising a primary sequence of SEQ. ID NO. 1 or a secondary sequence having at least 80% sequence identity to the primary sequence or an immunogenic fragment of the primary sequence or the secondary sequence comprising at least eight amino acids; a nucleic acid molecule consisting of a nucleic acid sequence encoding a polypeptide comprising a primary sequence of SEQ. ID NO. 8 or a secondary sequence having at least 80% sequence identity to the primary sequence or an immunogenic fragment of the primary sequence or the secondary sequence comprising at least eight amino acids; and a nucleic acid molecule consisting of a nucleic acid sequence encoding a polypeptide comprising a primary sequence of SEQ. ID NO. 9 or a secondary sequence having at least 80% sequence identity to the primary sequence or an immunogenic fragment of the primary sequence or the secondary sequence comprising at least eight amino acids; and
  iii) a cocktail of: a nucleic acid molecule consisting of a nucleic acid sequence encoding a polypeptide comprising a primary sequence of SEQ. ID NO. 1 or a secondary sequence having at least 80% sequence identity to the primary sequence or an immunogenic fragment of the primary sequence or the secondary sequence comprising at least eight amino acids; a nucleic acid molecule consisting of a nucleic acid sequence encoding a polypeptide comprising a primary sequence of SEQ. ID NO. 8 or a secondary sequence having at least 80% sequence identity to the primary sequence or an immunogenic fragment of the primary sequence or the secondary sequence comprising at least eight amino acids; and a nucleic acid molecule consisting of a nucleic acid sequence encoding a polypeptide comprising a primary sequence of SEQ. ID NO. 10 or a secondary sequence having at least 80% sequence identity to the primary sequence or an immunogenic fragment of the primary sequence or the secondary sequence comprising at least eight amino acids,
wherein each polypeptide is less than 100 amino acids in length.

Conveniently, the or each immunogenic fragment has the sequence of any one of SEQ. ID NOS. 17 to 40.

According to a fifth aspect of the present invention, there is provided a pharmaceutical composition comprising a polypeptide of the invention, a nucleic acid molecule of the invention, a cocktail of polypeptides of the invention or a cocktail of nucleic acid molecules of the invention and a pharmaceutically acceptable adjuvant, diluent or excipient and optionally another therapeutic ingredient.

Preferably, the polypeptide, nucleic acid molecule, cocktail of polypeptides or cocktail of nucleic acid molecules is present in an amount of between 50 and 200 µg.

According to a sixth aspect of the present invention, there is provided a method of treatment or prophylaxis of cancer in a patient comprising administering the polypeptide of the invention, the nucleic acid molecule of the invention, the cocktail of polypeptides of the invention, the cocktail of nucleic acid molecules of the invention or the pharmaceutical composition of the invention to the patient.

According to a seventh aspect of the present invention, there is provided a polypeptide of the invention, a nucleic acid molecule of the invention, a cocktail of polypeptides of the invention, a cocktail of nucleic acid molecules of the invention or a pharmaceutical composition of the invention for use in medicine.

Advantageously, the polypeptide, nucleic acid molecule, cocktail of polypeptides, cocktail of nucleic acid molecules or pharmaceutical composition is for use in the treatment or prophylaxis of cancer.

According to an eighth aspect of the present invention, there is provided the use of a polypeptide of the invention, a nucleic acid molecule of the invention, a cocktail of polypeptides of the invention, a cocktail of nucleic acid molecules of the invention or a pharmaceutical composition of the invention for the manufacture of a medicament for the treatment or prophylaxis of cancer.

The terms "polypeptide", "peptide" and "protein" are used interchangeably herein to refer to a polymer of amino acid residues. The terms apply to amino acid polymers in which one or more amino acid residues is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogues and amino acid mimetics that have a function that is similar to the naturally occurring amino acids. Naturally occurring amino acids are those encoded by the genetic code, as well as those modified after translation in cells (e.g. hydroxyproline, gamma-carboxyglutamate, and O-phosphoserine). The phrase "amino acid analogue" refers to compounds that have the same basic chemical structure (an alpha carbon bound to a hydrogen, a carboxy group, an amino group, and an R group) as a naturally occurring amino acid but have a modified R group or modified backbones (e.g. homoserine, norleucine, methionine sulfoxide, methionine methyl sulphonium). The phrase "amino acid mimetic" refers to chemical compounds that have different structures from but similar functions to naturally occurring amino acids.

The term "fragment" as used herein in relation to a polypeptide means a consecutive series of amino acids that form part of the polypeptide. An "immunogenic fragment" of a polypeptide is a fragment as previously defined which is capable of eliciting an immune response, such as a T-cell response, when administered to an individual.

The terms "gene", "polynucleotides", and "nucleic acid molecules" are used interchangeably herein to refer to a polymer of multiple nucleotides. The nucleic acid molecules may comprise naturally occurring nucleic acids or may comprise artificial nucleic acids such as peptide nucleic acids, morpholin and locked nucleic acid as well as glycol nucleic acid and threose nucleic acid.

The term "nucleotide" as used herein refers to naturally occurring nucleotides and synthetic nucleotide analogues that are recognised by cellular enzymes.

The term "treatment" as used herein refers to any partial or complete treatment and includes: inhibiting the disease or symptom, i.e. arresting its development; and relieving the disease or symptom, i.e. causing regression of the disease or symptom.

In this specification, the percentage "identity" between two sequences is determined using the BLASTP™ ("Basic Local Alignment Search Tool," an algorithm that finds regions of similarity between biological sequences) algorithm version 2.2.2 (Altschul, Stephen Thomas L. Madden, Alejandro A. Schaffer, Jinghui Zhang, Zheng Zhang, Webb Miller, and. David J. Lipman (1997), "Gapped BLAST® and PSI-BLAST™: a new generation of protein database search programs", Nucleic Acids Res, 25:3389-3402) using default parameters. In particular, the BLAST algorithm can be accessed on the internet using the URL, www.ncbi.nlm.nih.gov/blast/.

BRIEF DESCRIPTION OF THE FIGURES

FIG. 16 is a graph showing T-cell responses against selected hTERT peptides in six melanoma cancer patients.

DETAILED DESCRIPTION OF THE INVENTION

Figure 1:
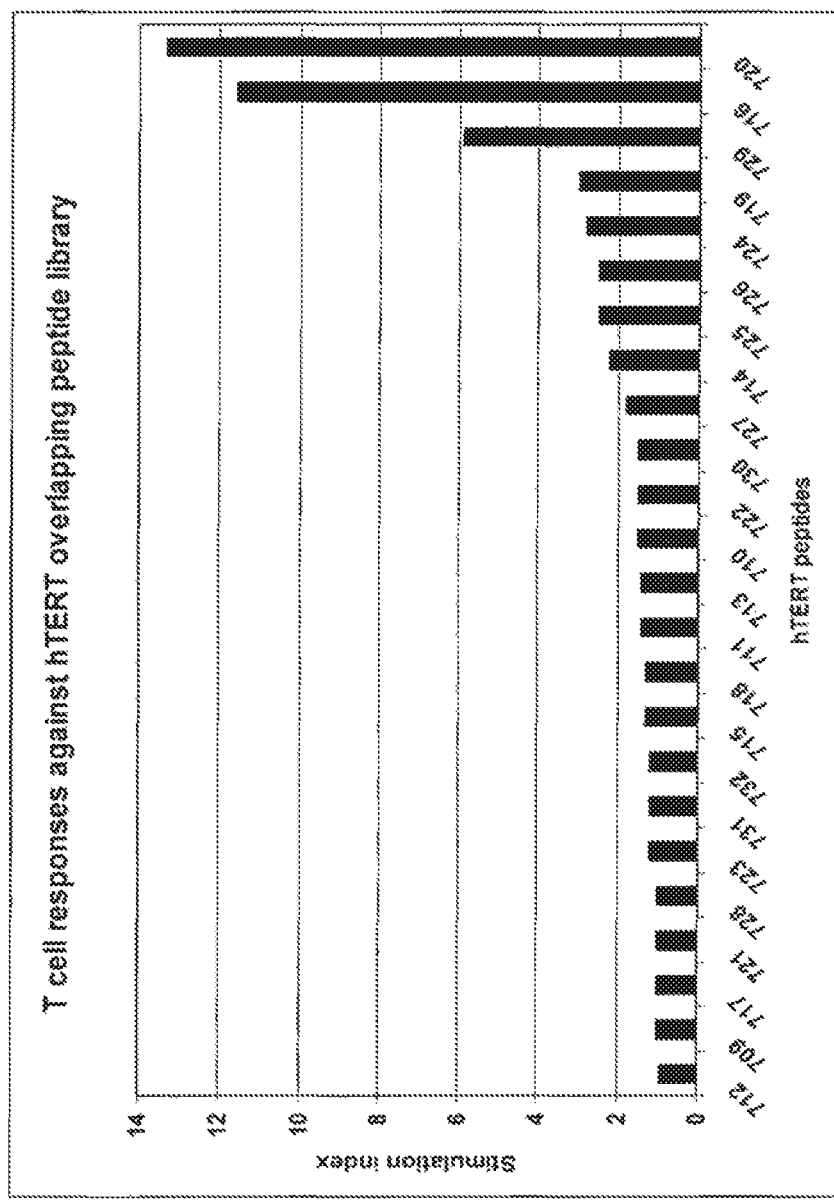
FIG. 1 is a bar graph summarising hTERT T-cell responses detected in pancreas cancer patient vaccinated with DC transfected with hTERT mRNA. In samples from various time points throughout a vaccination schedule, T-cell responses against 24 overlapping hTERT 15-mer peptides were detected. Proliferation in response to peptide-loaded PBMC was measured by $^3$H-thymidine incorporation. A stimulation index of >2 is considered an immune response.

In general terms, the invention relates to a polypeptide of the telomerase protein which comprise a sequence selected from SEQ. ID NOS. 2, 3, 4, 7, 8 and 9, wherein the polypeptide is less than 100 amino acids in length and does not comprise the sequence of polypeptide GV1001 (i.e. SEQ. ID NO. 10), SEQ. ID NO. 56 (reported by Schroers et al. 2002) any of SEQ ID NOS. 46, 57 or 59 to 61 (reported in WO03/038047) or SEQ ID NO. 62 (reported in WO00/02581). The polypeptide also does not consist of the sequence of SEQ ID NO. 58 (reported in WO03/038047).

Particularly preferred polypeptides comprise the sequence of SEQ. ID NO. 1 (which incorporates the sequences of SEQ. ID NOS. 2 and 3) SEQ. ID NO. 6 (which incorporates the sequences of SEQ. ID NOS. 8 and 9) and SEQ. ID NO. 7.

In some embodiments, the polypeptides consist of the sequences set out in one of SEQ. ID NOS. 1 to 9. In other embodiments, the polypeptides comprise one of the sequences set out in one of SEQ. ID NOS. 1 to 9 and any additional amino acids at the N and/or C termini are different from those present in the naturally occurring telomerase enzyme.

In other embodiments, there are provided immunogenic fragments of the aforementioned polypeptide, which fragments comprise at least eight amino acids and wherein the fragments are not any of the polypeptides of SEQ. ID NOS. 6 or 11 to 16 nor are the fragments polypeptides having the sequence of SEQ. ID NO. 56. Exemplary immunogenic fragments include those set out in SEQ. ID NOS. 17 to 40, which are predicted to have binding affinity for MHC molecules of certain HLA class I alleles. It is to be appreciated that the polypeptides of SEQ. ID NOS. 17 to 40 are all immunogenic fragments of the polypeptide of SEQ. ID NO. 1.

The sequence of the human telomerase enzyme (hTERT) is set out in GenBank accession no. AF015950. It is to be noted that each of SEQ. ID NOS. 1 to 9 is present within the amino acids at positions 660 to 705 of the telomerase enzyme. This corresponds to the active site of the human telomerase reverse transcriptase subunit. It is believed that, once an immune response to epitopes in this region of the reverse transcriptase subunit is elicited, any cells in a tumour in which the section of the telomerase gene encoding this region were mutated, and which could thereby avoid the immune response, would also have compromised the enzymatic activity of the encoded telomerase protein. Thus by targeting this region of the telomerase enzyme, it is less likely that a colony of cancerous cells could survive by mutation of the telomerase gene.

In some embodiments, a plurality of polypeptides as defined above are covalently linked with each other to form a large polypeptide or even a cyclic polypeptide.

In the above described embodiments of the invention, a polypeptide of a single sequence is provided. However, in other embodiments, a cocktail (i.e. a mixture) of polypeptides is provided where the cocktail comprises at least two different polypeptides comprising sequences from SEQ. ID NOS. 2 to 7. In some embodiments the cocktail comprises immunogenic fragments of said polypeptides, wherein the immunogenic fragments comprise at least eight amino acids. The polypeptides are less than 100 amino acids in length.

It is particularly preferred that the polypeptides in the cocktail comprise the sequences of SEQ. ID NOS. 1, 7, 8 or 9. It is especially preferred that the polypeptides in the cocktail comprise the sequences of SEQ. ID NOS. 1, 7 and 9; SEQ. ID NOS. 1, 8 and 9; or SEQ. ID NOS. 1, 8 and 10. It is thus within the scope of the invention that one of the polypeptides in the cocktail comprises the sequence of SEQ. ID NO. 10 (i.e. the sequence of the peptide referred to as GV1001). It is preferred that the immunogenic fragments are those of SEQ. ID NOS. 17 to 40.

It is preferred that the at least two polypeptides are different in the sense of being based on different sequences selected from SEQ. ID NOS. 1 to 10.

It is particularly preferred that in the cocktail of polypeptides, the polypeptides in the cocktail are capable of being bound by MHC molecules of more than one HLA allele. For example, in one embodiment, the cocktail comprises a first polypeptide that is capable of being bound by MHC molecules of allele HLA-A*0201 and a second polypeptide that is capable of being bound by MHC molecules of allele HLA-A-A*03. It is also to be understood that in some embodiments the cocktail comprises more than two polypeptides having different sequences (e.g. 3, 4 or 5 polypeptides).

In further embodiments, the or each polypeptide provided does not have exact sequence identity to one of the aforementioned polypeptides. Instead, the polypeptide has at least 80% sequence identity to the polypeptide set out above. It is particularly preferred that the sequence has at least 90%, 95% or 99% sequence identity to that set out above. It is also preferred that any addition or substitution of amino acid sequence results in the conservation of the properties of the original amino acid side chain. That is to say the substitution or modification is "conservative".

Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side chain (S, T, Y); a sulphur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are conservative substitutions for one another (see e.g. Creighton, Proteins (1984):
1) Alanine (A), Glycine (G);
2) Aspartic acid (D), Glutamic acid (E);
3) Aspargine (N), Glutamine (Q)
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

In some embodiments, the sequence of the or each polypeptide is altered in order to change (e.g. increase) the binding affinity of a polypeptide to an MHC molecule of a particular HLA allele. In other embodiments, the polypeptide has further amino acids, in addition to those set out above, at the N- and/or C-terminal thereof. Such additional amino acids can also be used to alter (e.g. increase) the binding affinity of a polypeptide to an MHC molecule.

It is necessary that the or each polypeptide (in particular a polypeptide whose sequence has been altered as set out above) is able to induce a cytotoxic T-lymphocyte ("CTL") response. That is to say the polypeptide should be able to induce CTLs when the polypeptide is presented by antigen presenting cells (e.g. dendritic cells).

Confirmation of CTL inducibility can be accomplished by inducing antigen-presenting cells carrying human MHC antigens (for example, B-lymphocytes, macrophages or dendritic cells) or more specifically dendritic cells derived from human peripheral blood mononuclear leukocytes, and after stimulation with the polypeptides, mixing with CD8+ ells, and then measuring the IFN-gamma produced and released by CTL against the target cells. As the reaction system, transgenic animals that have been produced to express a human HLA antigen (for example, those described in Ben-Mohamed L, Krishnan R, Longmate J, Auge C, Low L, Primus J, Diamond D J, Hum Immunol 61(8): 764-79, 2000 August, Related Articles, Books, Linkout Induction of CTL response by a minimal epitope vaccine in HLA A*0201/DR1 transgenic mice: dependence on HLA class II restricted T(H) response) can be used. For example, the target cells can be radiolabeled with $^{51}$Cr, and cytotoxic activity can be calculated from radioactivity released from the target cells. Alternatively, CTL inducibility can be examined by measuring IFN-gamma produced and released by CTL in the presence of antigen-presenting cells that carry immobilized peptides, and visualizing the inhibition zone on the media using anti-IFN-gamma monoclonal antibodies.

In some further embodiments of the present invention, the or each polypeptide is linked to other substances, while retaining their capability of inducing a CTL response. Such other substances include lipids, sugar and sugar chains, acetyl groups, natural and synthetic polymers and the like. The polypeptide, in certain embodiments, contains modifications such glycosylation, side chain oxidation or phosphorylation.

In some further embodiments, the or each polypeptide is produced by conventional processes known in the art. Alternatively, the polypeptide is a fragment of a telomerase protein produced by cleavage, for example, using cyanogen bromide, and subsequent purification. Enzymatic cleavage may also be used. In further embodiments, the polypeptide is in the form of a recombinant expressed polypeptide. For example, a suitable vector comprising a polynucleotide encoding the polypeptide in an expressible form (e.g. downstream of a regulatory sequence corresponding to a promoter sequence) is prepared and transformed into a suitable host cell. The host cell is then cultured to produce the polypeptide of interest. In other embodiments, the polypeptide is produced in vitro using in vitro translation systems.

In an alternative embodiment of the present invention, there is provided a nucleic acid molecule consisting of a nucleotide sequence encoding a polypeptide as set out above.

In further embodiments of the present invention, there is provided a cocktail (that is to say a mixture) of nucleic acid molecules wherein the cocktail comprises at least two different nucleic acid molecules comprising a nucleotide sequence encoding a polypeptide of the sequence of SEQ. ID NOS. 2 to 7. In alternative embodiments, the polypeptide is a fragment of one of SEQ. ID NOS. 2 to 7 comprising at least eight amino acids. In alternative variants, the sequence of the polypeptide is not identical to that aforementioned but instead has at least 80% sequence identity thereto. In any case, the polypeptide is less than 100 amino acids in length. It is preferred that the encoded polypeptide comprises the sequence of SEQ. ID NOS. 1, 7, 8 or 9. It is especially preferred that the encoded polypeptides in the cocktail comprise the sequences of SEQ. ID NOS. 1, 7 and 9; SEQ. ID NOS. 1, 8 and 9 or SEQ. ID NOS. 1, 8 and 10. In some embodiments, one encoded polypeptide thus comprises the sequence of SEQ. ID NO. 10 (i.e. the sequence of the GV1001 peptide). It is also preferred that the immunogenic fragments that are encoded are of the sequences of SEQ. ID NOS. 17 to 40. It is preferred that the at least two nucleic acid molecules are different in the sense of being based on different sequences selected from SEQ. ID NOS. 1 to 10.

It is to be appreciated that, owing to the degeneracy of the genetic code, nucleic acid molecules encoding a particular polypeptide may have a range of polynucleotide sequences. For example, the codons GCA, GCC, GCG and GCT all encode the amino acid alanine.

The nucleic acid molecules may be either DNA or RNA or derivatives thereof.

In further embodiments of the present invention, there is a pharmaceutical composition which comprises a polypeptide, a nucleic acid molecule or a cocktail of polypeptides or nucleic acid molecules as described above. In addition, the pharmaceutical composition comprises a pharmaceutically acceptable adjuvant, diluent or excipient. In certain embodiments the pharmaceutical composition comprises a mixture of a polypeptide of the invention and a nucleic acid molecule of the invention.

Exemplary adjuvants include Freund's complete or incomplete adjuvant, aluminium phosphate, aluminium hydroxide, alum, cholera toxin and salmonella toxin. A particularly preferred adjuvant is GM-CSF (granulocyte macrophage colony stimulating factor). Exemplary diluents and excipients include sterilised water, physiological saline, culture fluid and phosphate buffer.

The polypeptide or nucleic acid molecule is, in certain embodiments, coupled to an immunogenic carrier. Exemplary immunogenic carriers include keyhole limpet haemocyanin, bovine serum albumin, ovalbumin and fowl immunoglobulin.

The pharmaceutical composition, in some embodiments, also comprises a further therapeutic ingredient. Exemplary further therapeutic ingredients include interleukin-2 (IL2), interleukin-12 (IL2), a further telomerase polypeptide (that is to say a polypeptide of the telomerase enzyme aside from those discussed above) chemotherapeutics, pain killers, anti-inflammatory agents and other anti-cancer agents.

In some embodiments the pharmaceutical composition comprising a polypeptide is provide in the form of a lipopeptide conjugate which is known to induce a high-affinity cytotoxic T-cell response (Deres, 1989, *Nature* 342).

Further details of additional components of the pharmaceutical composition may be found in Remington's Pharmaceutical Sciences and US Pharmacopoeia, 1984, Mack Publishing Company, Easton, Pa., USA.

In use, the polypeptide, nucleic acid molecule, the peptide cocktail, nucleic acid molecule cocktail or pharmaceutical composition, as explained above (hereinafter, the "medicament") is administered to a patient in need of treatment. Alternatively, the product is administered to an individual prior to any symptoms of cancer in order to provide protective immunity against cancer.

In embodiments in which the medicament comprises a polypeptide, the polypeptide is endocytosed by antigen presenting cells, may be subject to antigen processing and is then presented in complex with an MHC class I or class II molecule on the cell surface. Through interaction with T-cell receptors on the surface of T-cells, a CD4+ or CD8+ T-cell response is elicited. In embodiments in which the medicament comprises a nucleic acid molecule, the nucleic acid molecule is also endocytosed and is then transcribed (if the nucleic acid molecule is DNA), and the encoded polypeptide is synthesised through endogenous cellular pathways. Subsequently, the encoded polypeptide is processed and presented on an MHC molecule in order to elicit the T-cell response, as previously described. Thus the medicament may be used as a vaccine in order to elicit either CD4+ or CD8+ T-cell immunity.

In principle, any mode of administration of the medicament may be used but injection is particularly preferred. For example the medicament may be injected directly into a tumour in a patient. However, if the cancer to be treated is in the nose or mouth of a patient then in some embodiments the medicament is administered by spray and inhalation.

A suitable dosage for the medicament is from 50-200 μg although dosages outside this range may occasionally be required (e.g. from 1-500 μg). A dosage of between 100 and 150 μg is particularly preferred. The medicament is, in some embodiments, administered to the patient weekly or monthly. In certain embodiments, an "aggressive" treatment regimen is pursued which comprises three administrations of the medicament in the first week of treatment, then weekly administrations for a month, then monthly administrations for six months followed by a single administration every six months.

In principle, the medicament may be admitted to a patient suffering from any type of cancer in which the telomerase gene is activated. Such cancers include but are not limited to breast cancer, prostate cancer, pancreatic cancer, colorectal cancer, lung cancer, malignant melanoma, leukaemias, lymphomas, ovarian cancer, cervical cancer and biliary tract carcinomas. As previously stated, the telomerase enzyme is expressed in the vast majority of cancers so the efficacy of the medicament of the present invention is not limited to any particular type of cancer.

It is to be appreciated that, depending upon the class of T-lymphocyte response to be elicited, different lengths of polypeptide are preferred. More specifically, in order to elicit a CD8+ T-cell response, the polypeptide must be presented on MHC class I molecules which will typically only bind polypeptides which are between 8 and 10 amino acid residues in length. On the other hand, in order to elicit a CD4+ T-cell response, it is necessary for the polypeptide to be presented on an MHC class II molecule for which the polypeptides may generally be longer, typically between 15 and 24 amino acid residues in length. It is to be noted that some of the polypeptides of the present invention (e.g. the polypeptide of SEQ. ID NO. 1) are longer than would normally be accommodated in either an MHC class I or class II molecule. Peptides of this length have been shown to induce more robust immune responses, e.g by groups working on HPV and cervical cancer vaccination (Welters et al, 2008). Without wishing to be bound by theory, it is believed that such polypeptides, following their administration to a patient, are endocytosed by cells, subjected to proteolytic degradation in the proteasome and then presented on an MHC class I or class II molecule. Thus such polypeptides may give rise to an MHC class I and/or an MHC class II restricted T-cell response. It is also to be appreciated that longer polypeptides remain extant within a patient for a greater period of time than shorter polypeptides and therefore there is a longer period of time during which they may elicit an immune response. This is particularly significant as regards those polypeptides which have a relatively low MHC binding affinity.

It is also to be appreciated that the telomerase enzyme is a "self protein", that is to say, the enzyme is a naturally-occurring protein in the human body. Accordingly, individuals will generally have developed some degree of immunological tolerance to polypeptides of the telomerase enzyme through a process whereby T-cells reactive with such polypeptides are destroyed in the thymus of the individual during T-cell development. Thus in some embodiments of the present invention, polypeptides of the present invention with a relatively low MHC binding affinity are desired. This is because polypeptides with lower MHC binding affinity will have been exposed to maturing T-cells at a lower rate and so it is less likely that all of the individual's T-cells reactive with the polypeptide will have been deleted from the individual's T-cell repertoire. Thus polypeptides having a relatively low MHC binding affinity are, in some embodiments, able to overcome immunological tolerance more readily.

In some embodiments of the invention, the administration of one of the polypeptides of the invention results in "epitope spreading" whereby an immune response is elicited against other polypeptides of the telomerase protein which are adjacent to the administered polypeptide in the telomerase protein.

EXAMPLES

Example 1 hTERT epitopes that were recognized by a patient's T cells following vaccination with hTERT transfected DCs were characterised. Vaccination resulted in a diverse and broad immune response involving both CD4+ Th cells and CD8+ T cells. This response is believed to be responsible for the tumour regression and long term survival observed in the patient.

Material and Methods

Patient

A 62-year old woman with recurrent ductal adenocarcinoma of the pancreas was vaccinated with dendritic cells loaded with hTERT mRNA on a compassionate use basis. The treatment was approved by the Norwegian Medicines Agency and the Regional Committee for Medical Research Ethics. It was performed in compliance with the World Medical Association Declaration of Helsinki. Written informed consent was obtained from the patient.

Production of mRNA-transfected DCs

DCs were generated as described earlier (Kyte et al, 2006 and Mu L J et al 2003). Briefly, monocytes obtained from leukapheresis product were cultured for 5 days with granulocyte-macrophage colony-stimulating factor (GM-CSF) and interleukin-4 (IL-4). The resulting immature DCs were transfected with hTERT-mRNA by square wave electroporation (Kyte et al, 2006, Sæbøe-Larssen S et al 2002) and then cultured for 2 days with cytokines facilitating maturation (interleukin-1β (IL-1β), interleukin-6 (IL-6), tumor necrosis factor α (TNFα) and prostaglandin $E_2$ (PGE2)). To obtain adequate control DCs, a fraction of the DCs was mock-transfected, i.e. electroporated without mRNA. The DC phenotype was evaluated by flow cytometry, as previously described (Kyte et al, 2006). The DCs had a mature DC phenotype, expressing HLA class II, CD86 and CD83, but not CD14. The DC viability was >85%, as assessed by trypan blue staining.

The second and third vaccine batch were fast DC (Alldawi et al 2005, Tanaka et al 2006, Ho et al 2006). Monocytes were cultured for 2 days with GM-CSF and IL-4, then matured for 1 day in the same way as for conventional DC before electroporation. The DCs were then left overnight before being frozen.

Vaccine

The vaccine consisted of $5 \times 10^6$ autologous monocyte-derived dendritic cells loaded with hTERT mRNA. The patient received 4 weekly injections followed by monthly booster injections.

Clinical Monitoring

Adverse events were recorded and graded according to the NCI-common toxicity criteria, as previously reported (Kyte et al, 2006 Gene therapy). Only minor side effects were observed, with no treatment related grade III-IV toxicity. Objective tumour response was assessed by clinical examination and CT scans prior to start of vaccination and every 3 months during the vaccination. The tumour response was classified according to the Response Evaluation Criteria in Solid Tumors (RECIST) (Therasse P et al, 2000).

DTH

Immunomonitoring

Peripheral blood mononuclear cells (PBMCs) were obtained prior to the four standard vaccinations, after 5 weeks and after 12 weeks. PBMCs were also obtained before each monthly booster vaccination. The PBMCs were isolated and frozen as previously described (Kyte et al, 2005). Thawed PBMCs were stimulated once in vitro with tDCs (not with mockDCs) and cultured and then tested in T cell proliferation assays ($^3$H Thymidine) as previously described (Kyte et al 2006). The T cells were tested in triplicates. Irradiated tDCs and mock-transfected DC controls (mockDCs) were used or PBMC with or without hTERT peptide as APCs. Negative controls with T cells only were included.

PBMCs from various time points were stimulated with an overlapping hTERT 15-mer peptide library or a 30-mer hTERT peptide, all from ProImmune and then tested in proliferation assays as above using irradiated PBMCs as APCs as described in (Bernhardt et al 2006).

Flow Cytometry

Pentamer staining was performed on fresh or frozen patient PBMCs. Phycoerythrin-conjugated pentamers were manufactured by ProImmune and tested for non-specific staining on HLA-A2 positive T-cell lines specific for Choriomeningitis Virus (CMV) peptide NLVPMTATV. Manufacturer's recommended working concentration was used. Pentamer with HIV peptide SLYNTVATL-A*0201 was used as a negative control. Cells were stained with pentamers for 10 min at room temperature (RT), washed in staining buffer consisting of phosphate buffered saline (PBS) containing 0.1% Human serum albumin (HSA) and 0.1% sodium azide. Cells were then stained anti-CD4-Fluorescein isothiocyanate (FITC), anti-CD19-FITC (eBioscience), anti-CD8-PerCP and anti-CD3-Pacific Blue (PB) (eBioscience) for 15 min at RT, washed once in staining buffer and resuspended in the same buffer before acquisition. For intracellular staining, 12-day peptide stimulated T cells were stimulated overnight in the presence of Brefeldin A (BD Bioscience) at 10 ug/ml and BD GOLGISTOP® (a protein transport inhibitor containing monensin) (BD Biosciences) at a 1/1000 dilution with an autologous Epstein Barr Virus-transformed B lymphoblastoid cell lines (EBV-LCL) loaded with peptide at a T cell to target ratio of 5:1. Non-peptide loaded target cells and T cells alone were used as negative controls. Cells were then stained for CD3 (eBioscience), CD4, CD8, IFN- (eBioscience), IL-2 and TNF-α using the BD Cytofix/Cytoperm kit according to the manufacturer's instructions. Finally, cells were resuspended in staining buffer containing 1% paraformaldehyde. All antibodies and all reagents for intracellular cytokine staining were purchased from BD Pharmingen except where noted. 250,000 lymphocytes were acquired per sample using a BD LSR II flow cytometer and data was analyzed using FLOWJO® (a software package for analyzing flow cytometry data) software (Treestar Inc., Ashland, Oreg., USA).

Results

The patient experienced disease stabilization on gemcitabine treatment, but after 5 months the treatment was suspended due to adverse effects. She was then offered DC vaccination as an alternative treatment. After 18 months of vaccination she experienced complete remission which is maintained after 30 months of vaccination (44 months post diagnosis). The patient was re-diagnosed and examined by an independent pathologist who confirmed the diagnosis of ductal adenocarcinoma.

The median survival for inoperable pancreas cancer patients is 8-10 months, which in this case is far exceeded. The first vaccine batch consisted of $5 \times 10^6$ conventional DCs (Kyte et al 2006) and the patient had 15 vaccines administered. Due to the demonstration of an immune response against the vaccine and stable disease new vaccine batches were made and batches 2 and 3 were fast DC and 10 and 17 vaccines, respectively, of $5 \times 10^6$ DCs loaded with hTERT mRNA were administered.

A proliferative T-cell response to the DC vaccine could be measured in vitro 3 months post vaccination and stabilized from month 6. Having documented the presence of an immune response to hTERT transfected DCs, it was desired to investigate which hTERT epitopes were responsible for inducing the immune response. This was tested by measuring T-cell proliferation to a hTERT peptide library (FIG. 1) and ex vivo pentamer staining of PBMCs.

Figure 2:
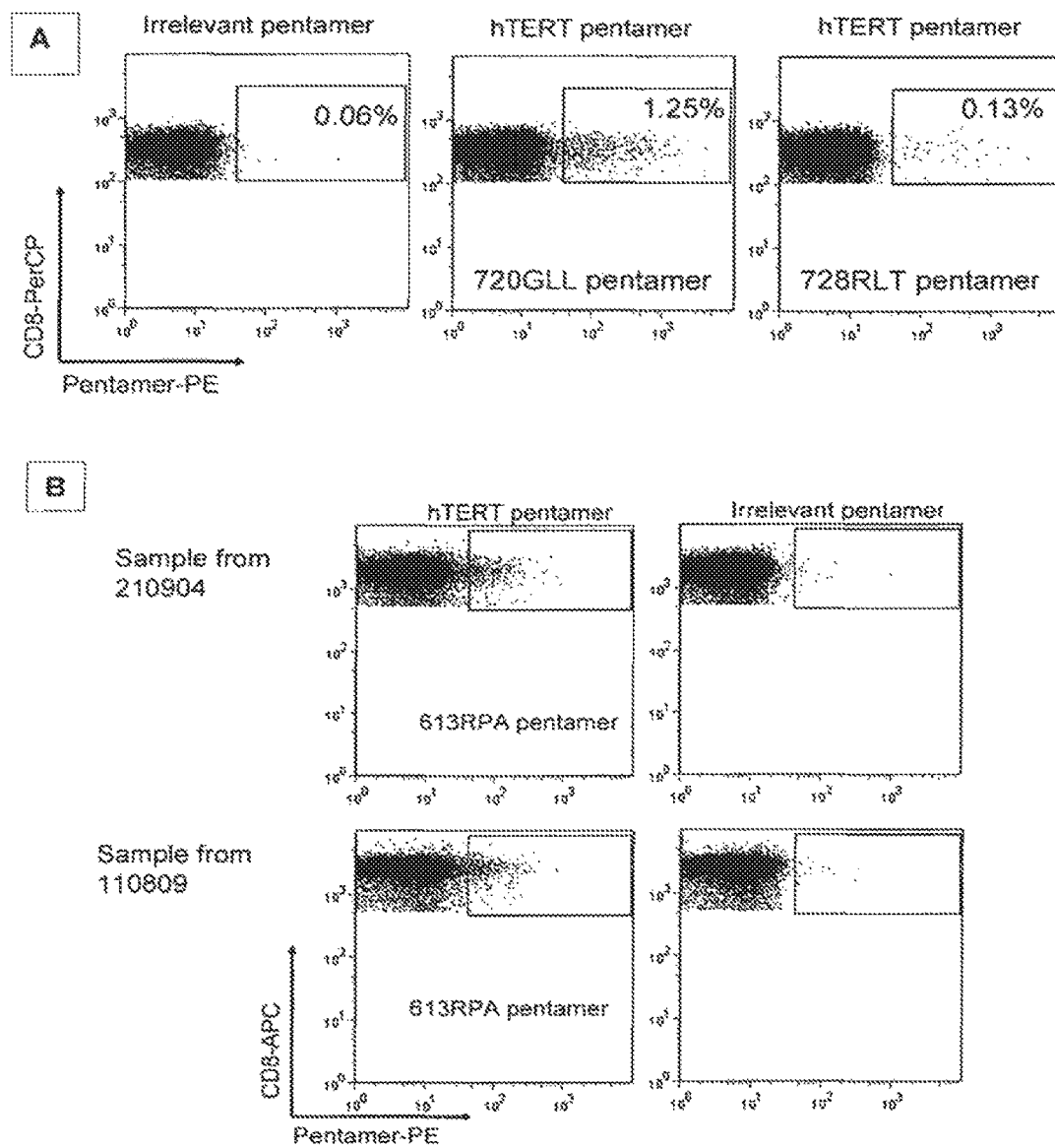
FIG. 2 is a series of diagrams showing the detection of hTERT-specific HLA-A2 restricted CD8+ T cells by flow cytometry in vaccinated cancer patients. PBMC were stained directly after isolation without prior antigen stimulation. Pentamer staining is shown in cells gated on CD8+ CD3+ cells. Background staining shown in plot with irrelevant pentamer (HIV-peptide), hTERT pentamer plots show staining for two novel hTERT peptides in a pancreas cancer patient (A) (the peptide referred to as 720GLL corresponds to SEQ. ID NO. 3; the peptide referred to as 728RLT corresponds to SEQ. ID NO. 6) and for a third hTERT peptide detected in a lung cancer patient (B) (the peptide referred to as 613RPA corresponds to SEQ. ID NO. 5), the latter at two different time points, five years apart. 45 000 CD8+ T cells were analysed.

Proliferative T-cell responses were detected in six of the 15-mer hTERT peptides from the overlapping peptide library and a 30-mer hTERT peptide. The presence of hTERT-pentamer positive CD8+ T cells was detected both pre- and post-vaccination with percentages ranging from 0.15% to 1.25% in non-stimulated PBMCS A population of 1.25% of the CD8+ T cells was shown to be pentamer-positive in fresh PBMCs 24 months post vaccination (FIG. 2A) and increased to approximately 3% after in vitro peptide stimulation (data not shown).

After one round of in vitro stimulation with the 30-mer hTERT peptide containing at least two T helper epitopes as well as the CTL epitopes in the 720GLL-pentamer, we could detect a small population of multifunctional CD4+ T cells, secreting IFN-γ, IL-4 and TNF-α in response to autologous EBV-transformed B-cells loaded with the same peptide. There was no difference in the CD8+ T cell population after stimulation with the peptide-loaded target cells compared with those stimulated with non-peptide loaded targets (data not shown). High background levels of IL-2 seen may be due to some stimulation given by the transformed B cell line which could express hTERT. Unfortunately, due to the limited amount of T cells in each experiment additional functional assays could not be performed.

Discussion

In this Example, there is reported a pancreas cancer patient with an extraordinary disease course following treatment with chemotherapy and vaccination with autologous DC transfected with hTERT mRNA.

The patient described here has survived for more than 4 years with a relapsing pancreatic adenocarcinoma following radical surgery. To confirm that the original diagnosis was correct the primary tumour was re-diagnosed by an independent pathologist.

Following radical surgery in January 2006 the patient relapsed in December 2006 with enlarged lymph nodes localized in liver hilus, truncus iliacus and in the retroeritoneum as assessed by CT.

The patient responded well to chemotherapy and CT scans revealed tumour shrinkage. However, after 5 months with chemotherapy the patient developed severe adverse effects and the treatment was stopped.

In this clinical setting, the patient was offered treatment with autologous DC loaded with hTERT mRNA vaccination on a compassionate use basis in order to consolidate the beneficial effect of the chemotherapy.

Interestingly, rather than developing progressive disease after chemotherapy ended, a long term disease stabilization and potentially complete remission was obtained. Two consecutive PET scans 6 months apart, revealed a metabolically silent tumour tissue at the site of pancreatic and metastatic lesions. These intriguing findings indicate that the immunotherapeutic strategy used has induced a clinically relevant immune response in this patient. It was therefore important to document and study in depth the immune response against hTERT in the patient. Furthermore, as there is a complete lack of information regarding the detailed immune response to hTERT from studies using full length hTERT mRNA for vaccination, it is important to identify clinically relevant hTERT epitopes for the development of the next generation of hTERT vaccines.

A high frequency of CD8+ T cells binding pentamers with new CTL epitopes was found. These two epitopes were HLA-A*0201 restricted and have not been previously described. Interestingly, the 9-mer epitope (720GLL, SEQ. ID NO. 3) is embedded in a 15-mer peptide (720, PGLL-GASVLGLDDIH—SEQ. ID NO. 55) which is the same length as peptide R672 (SEQ. ID NO. 56) previously described by Schroers et al 2002, but shifted one amino acid towards the C-terminus of hTERT. It is possible, therefore, that the same amino acid residues within both 15-mer peptides are responsible for the T-cell response. Importantly, the same 15-mer peptide (720) was also recognized by T cells from the patient reported here in the proliferation assays, indicating that this peptide fragment of hTERT may have elicited both a CD4+ and a CD8+ T cell response in this patient. Moreover, five other 15-mer peptides were recognized by T cells from this patient. Three of these peptides have not previously been reported. Taken together, these results demonstrate that this vaccine has induced T-cell responses to at least 10 different hTERT epitopes in this patient. The number of epitopes may be considerably greater as only a limited number of peptides were used from an overlapping peptide library not covering the whole sequence as well only a few pentamers limited to HLA-A*0201 presented peptides.

This indicates that there is no widespread tolerance against hTERT peptides and that the vaccination strategy using hTERT mRNA transfected DCs is highly potent.

The above results also demonstrate that T cells from this patient, capable of recognizing a 30-mer hTERT peptide encompassing two of the 15-mer and one 9-mer peptide, produce three Th1-associated cytokines simultaneously. This kind of multifunctionality has previously been demonstrated to give better protection against infection. Darrah et al, 2007 showed that the degree of protection against *Leishmania major* infection in vaccinated mice is predicted by the frequency of CD4+ T cells simultaneously producing interferon-γ (IFN-, interleukin-2 and TNF-α).

The very unusual clinical course of this patient indicates that the vaccination and the resulting immune response may have had an impact on the tumour and the metastases. This is highly conceivable as it has been demonstrated that a broad and composite immune response against hTERT was elicited by the hTERT mRNA DC vaccine. As a result an immune attack on remaining tumour cells may have involved direct killing of tumour cells by hTERT-specific CTLs, T helper cell cytokine production (IFN-γ, TNF-α) effects on cancer cells and tumour-associated stroma and tumour neovasculature and amplification of an ongoing spontaneous immune responses against other tumour antigens present in the adenocarcinoma. This can take place when hTERT-specific Th cells encounter MHC class II positive antigen presenting cells that have taken up tumour antigens in situ or in tumour draining lymph nodes.

Example 2

Figure 12:
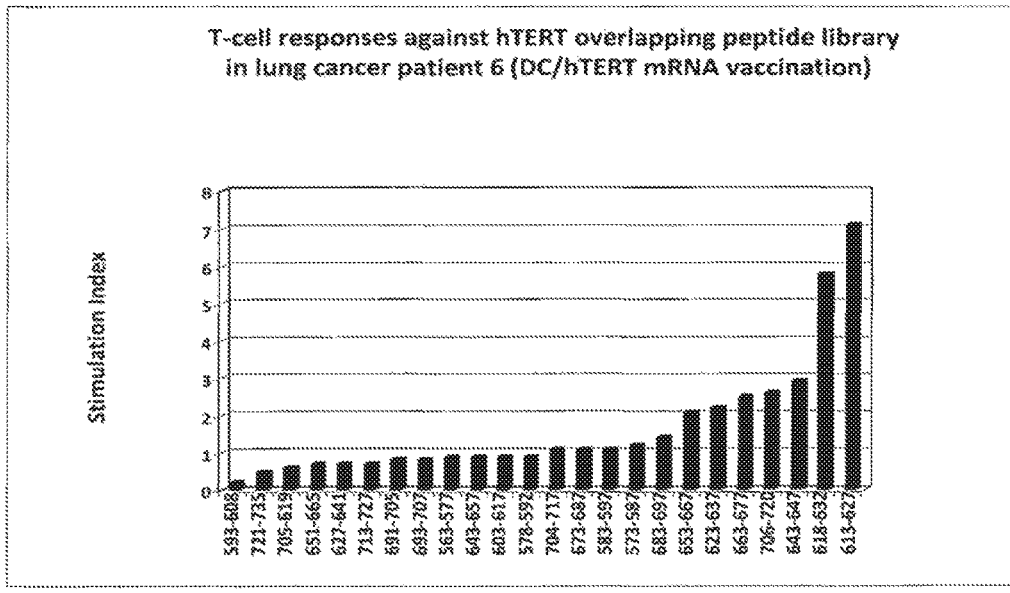
FIG. 12 is a graph showing T-cell response against hTERT overlapping peptide library in a lung cancer patient following vaccination with DC transfected with hTERT mRNA.
Figure 13:
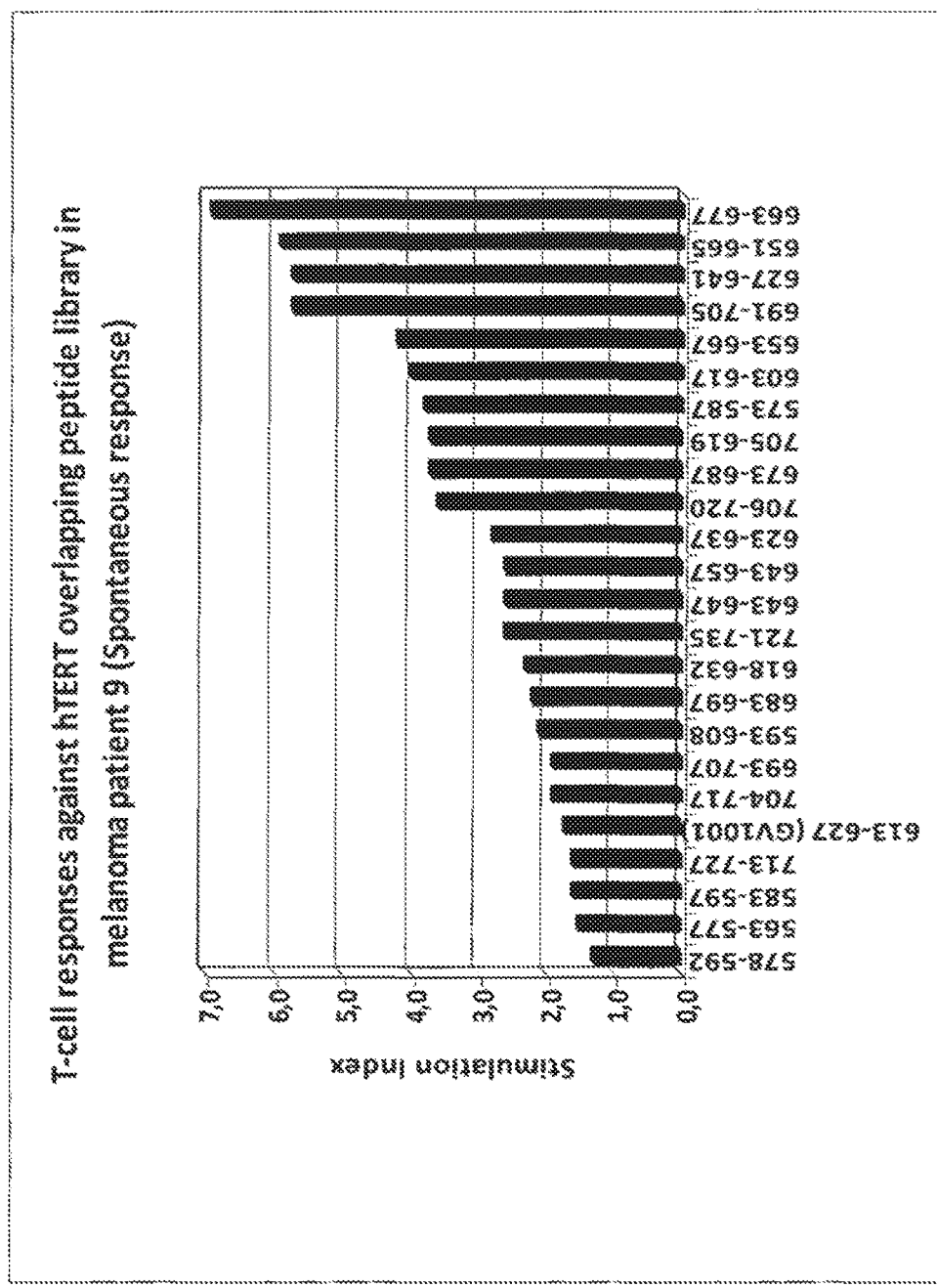
FIG. 13 is a graph showing spontaneous T-cell response against hTERT overlapping peptide library in a third melanoma patient who had not been vaccinated.

One stage IV lung cancer patient was vaccinated with autologous monocyte-derived DC transfected with mRNA encoding hTERT to investigate the safety, tolerability and immunological response prior to the start of a new phase I/II clinical trial. The patient first received four weekly vaccinations followed by monthly booster vaccinations of $5\times10^6$ DC injected intradermally. Peripheral blood mononuclear cells (PBMC) were obtained prior to the four standard vaccinations, after 5 weeks, 12 weeks and monthly thereafter. Thawed PBMC were stimulated in vitro with transfected DC. T-cell proliferation assays were performed with irradiated transfected DC and mock-transfected as DC controls. In addition, hTERT-specific CD8+ T cells were monitored by pentamer staining. The treatment was well tolerated with minor side effects and the patient experienced prolonged survival (72 weeks) compared with what would be expected (12 weeks). The patient showed specific T-cell proliferation in response to the mRNA-loaded DC in vitro after vaccination. Stable populations of hTERT-specific CD8+ T cells were detected by pentamer staining in post-vaccination samples. Samples from different time points post vaccination were further tested against a panel of 24 overlapping hTERT peptides and T-cell responses against multiple peptides were detected (FIG. 12). T-cell responses to these epitopes have also been identified both in non-vaccinated cancer patients and cancer patients previously vaccinated with the GV1001 telomerase peptide (SEQ. ID NO. 10), which indicates a high degree of immunogenicity and HLA promiscuity. These clinical experiences in Examples 1 and 2 show that vaccination with hTERT-mRNA transfected DC is safe and able to induce robust immune responses to several telomerase T-cell epitopes both in CD4+ and 008+ T cells.

Example 3

Figure 3:
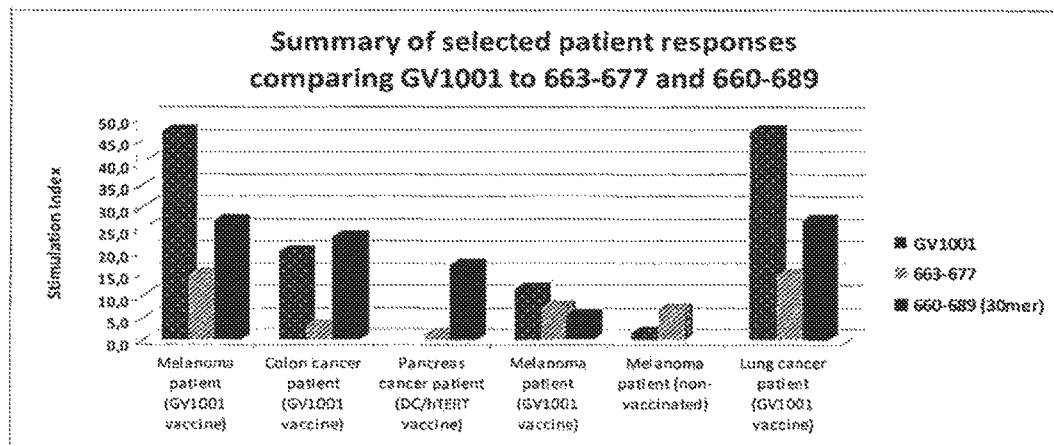
FIG. 3 is a graph showing T-cell proliferation in response to GV1001 peptide (SEQ. ID NO. 10), 663-677 (15-mer) (SEQ. ID NO. 2) and 660-689 (30-mer) (SEQ. ID NO. 1). Stimulation index is a measure of how many fold above background the peptide-specific proliferation is.

Peptides of the telomerase enzyme suitable for eliciting T-cell responses were identified and ranked by examining data from several vaccinated patients (vaccinated with either the GV1001 peptide or with dendritic cells transfected with mRNA encoding hTERT) and a non-vaccinated cancer patient, to identify peptides that would be able to induce useful anti-tumour immune responses. A summary of the selected patients, their vaccination status and their clinical response is provided in Table 9. In one patient vaccinated with GV1001 (SEQ. ID NO. 10), the T-cell response to peptide 660-689 (30-mer) (SEQ. ID NO. 1) is even stronger than to the vaccine peptide itself at certain time points (see FIG. 3), but also the other patients show robust immune responses to this peptide. The peptides identified are set out in Table 1. T cell responses against these peptides were not found in any of six normal blood donors that were tested for reactivity.

This is important in order to be able to induce strong immune response in vivo where peptide concentrations are lower.

The 30-mer polypeptide of SEQ. ID NO. 1 has shown reactivity in nearly all the cancer patients tested and therefore seems very immunogenic. This peptide contains both motifs that can be recognized by CD4+ T helper cells like the GV1001 vaccine (SEQ. ID NO. 10) and also motifs recognizable by CD8+ cytotoxic T lymphocytes (CTL). Both of these types of responses have been detected in vitro in T lymphocytes from patients stimulated with the peptide.

Figure 5:
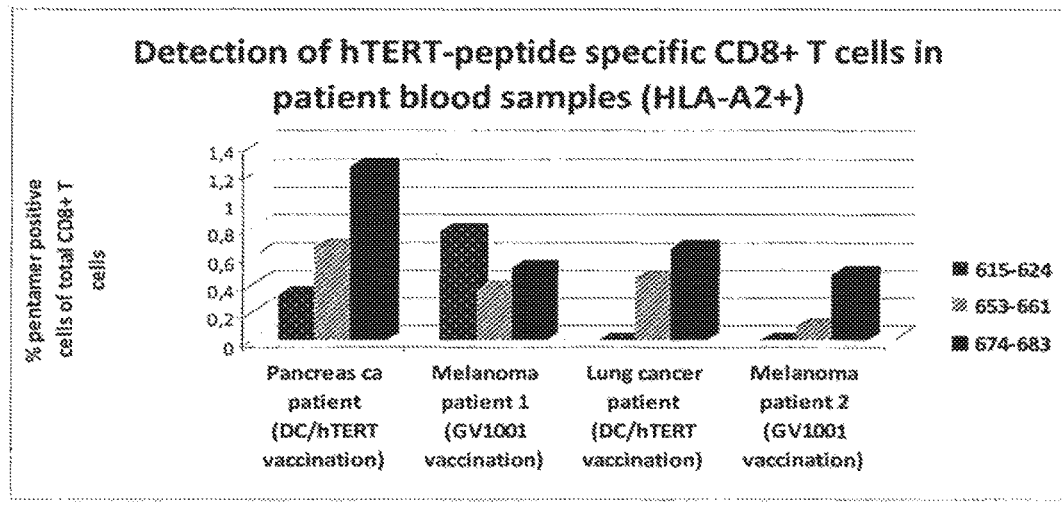
FIG. 5 is a graph showing the results of detection of CD8+ T lymphocytes specific for the 9- or 10-mer peptides of SEQ. ID NOS. 3, 4 and 6 directly in peripheral blood mononuclear cells (PBMC) from patient blood samples. The 615-624 peptide (SEQ. ID NO. 4) was not tested in the two last patients. The patients are HLA-A2+. Background staining with irrelevant pentamer was <0.05%.

Using fluorochrome-tagged reagents (pentamers) able to bind CD8+ T lymphocytes specific for the above-mentioned 9- or 10-mer peptides, the presence of these cells has been detected in numerous cancer patients, mainly vaccinated with GV1001 (SEQ. ID NO. 10). These 9- or 10-mer peptides are recognized when presented on HLA-A2 molecules (FIG. 5) which are present in approximately 50% of the Caucasian population and on HLA-B7 molecules (FIG. 6) present in 20% of the same population, which means that together they cover the majority of the Caucasian population.

TABLE 1

| SEQ. ID NO. | Peptide Name | Peptide Sequence | Former Peptide Name | No. of amino acids in peptide |
|---|---|---|---|---|
| 1 | 660-689 | ALFSVLNYERARRPGLLGASVLGLDDIHRA | 719-20 | 30 |
| 2 | 663-677 | SVLNYERARRPGLLG | 719 | 15 |
| 3 | 674-683 | GLLGASVLGL | 720GLL | 10 |
| 4 | 615-624 | ALLTSRLRH | 615ALL | 10 |
| 5 | 613-621 | RPALLTSRL | 613RPA | 9 |
| 6 | 653-661 | RLTSRVKAL | 728RLT | 9 |
| 7 | 691-705 | RTFVLRVRAQDPPPE | 725 | 15 |
| 8 | 653-667 | RLTSRVKALFSVLNY | 718 | 15 |
| 9 | 651-665 | AERLTSRVKALFSVL | 728 | 15 |

Figure 4:
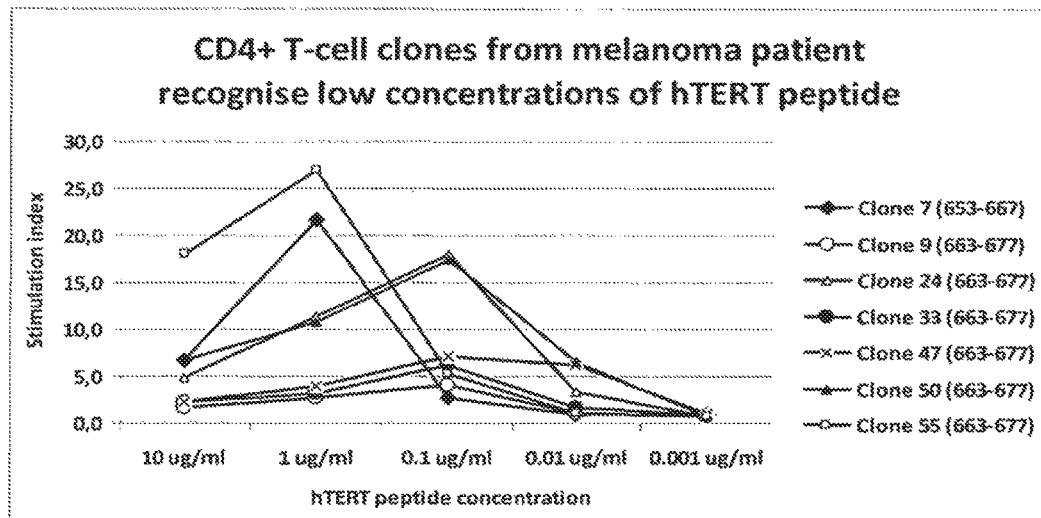
FIG. 4 is a graph showing the results of CD4+ T-cell clones demonstrating peptide-specific proliferation in response to decreasing peptide concentrations. A value above 2 is considered as a positive response.

T-cell clones specific for all of the peptides of 15- or 30-amino acids shown in Table 1 have also been obtained from patients. These clones have been shown to recognize naturally processed peptides (data not shown) and respond to very low peptide concentrations down to 10 ng/ml (see FIG. 4), which means they have high affinity for their target.

In addition, the 15- and 30-mer peptides listed in Table 1 show reactivity in nearly all patients tested, which means they are promiscuous with respect to the HLA class II alleles on which they are presented and that they are applicable to nearly the whole population without any need for HLA-screening (see Table 2).

TABLE 2

| HLA class II allele | Frequency in Caucasians | Specific clones | Peptide specificity | Patients | Cancer |
|---|---|---|---|---|---|
| DR*01 | 22.6% | T-cell lines | 663-677 | 2 | Malignant melanoma |
| DR*04 | 33.9% | 3 | 653-667, 663-677 | 3 | Malignant melanoma |
| DR*07 | 30.1% | 3 | Part of 660-689 | 1 | Colon cancer, Schroers et al, 2003 |
| DR*08 | 4.3% | >85 | 663-677 | 2 | Malignant Melanoma and Lung cancer |
| DR*14 | 2.9% | 6 clones | 660-689 | 2 | Colon cancer, Lung cancer |

As well as inducing reactivity in patients vaccinated with GV1001 (SEQ. ID NO. 10), these peptides have also induced T-cell responses in cells from one lung cancer and one pancreas cancer patient vaccinated with dendritic cells transfected with hTERT mRNA. The mRNA used will not give translation of the full-length hTERT protein, but covers the majority of it, and the peptides listed in Table 1 induce some of the strongest responses in these patients.

Example 4

T-cell responses to a hTERT peptide library (including the polypeptides from Table 1) were determined for T-cells from 5 patients in addition to the patients reported in Examples 1 and 2. The methods were the same as previously described in Example 1 or in Bernhardt et al 2006. In brief, PBMCs from various time points during vaccination were stimulated with the overlapping hTERT peptide library prior to testing for specific T-cell responses in proliferation assays. The results are shown in FIGS. 7 to 13. A complete list of peptides is shown in Table 3.

The histograms in FIGS. 7 to 13 show responses against the hTERT overlapping peptide library in 7 patients (the pancreas cancer patient was the one reported in Example 1).

Peptide 613-627 has a very similar sequence to GV1001 (SEQ. ID NO. 10) and is assumed to be recognized by the same cells that recognize GV1001, but peptide 613-627 is not identical to the vaccine peptide.

Figure 6:
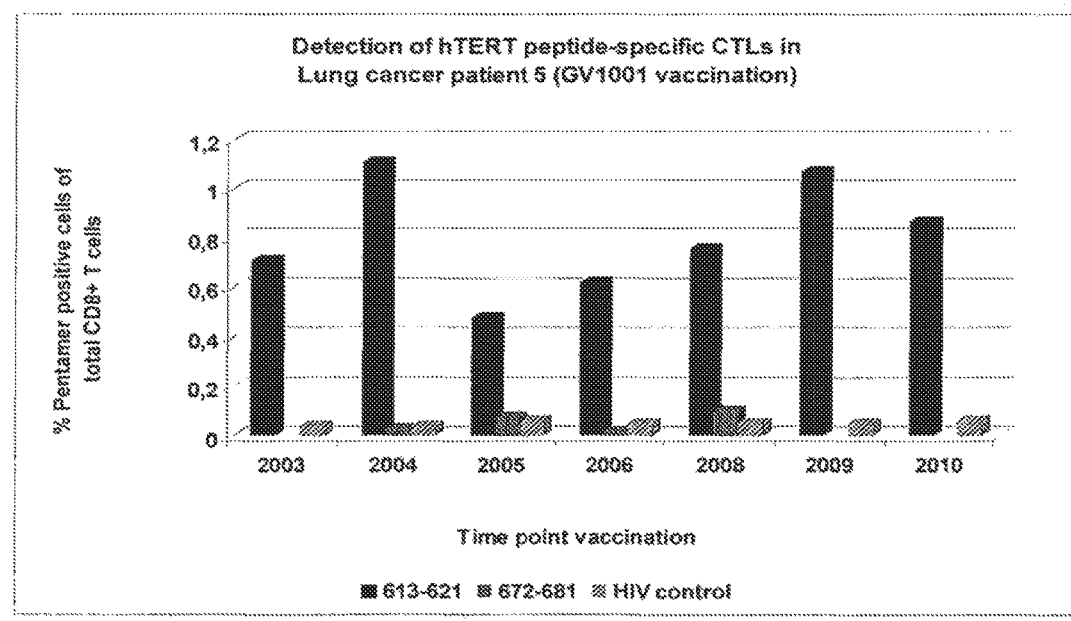
FIG. 6 is a graph showing the results of detection of CD8+ T lymphocytes specific for the 9-mer peptide 613-621 (SEQ. ID NO. 5) in a lung cancer patient who has been in complete remission for several years after GV1001 vaccination (SEQ. ID NO. 10). The patient is HLA-B7+. The patient has subsequently been vaccinated every 6 months and a stable CD8+ T cell population specific for hTERT peptide 613-621 can still be detected six years after the patient experienced complete remission. A second minor CTL population specific for another CTL epitope, 672-681 (SEQ ID. NO. 25), was detected at some time points.
Figure 7:
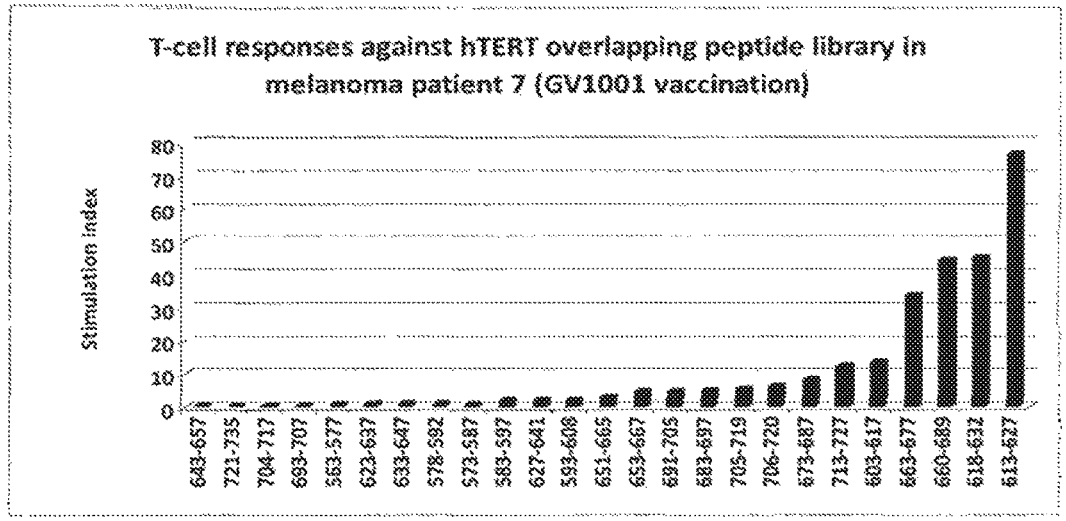
FIG. 7 is a graph showing T-cell response against hTERT overlapping peptide library in a melanoma patient following vaccination with GV1001 (SEQ. ID NO. 10).
Figure 8:
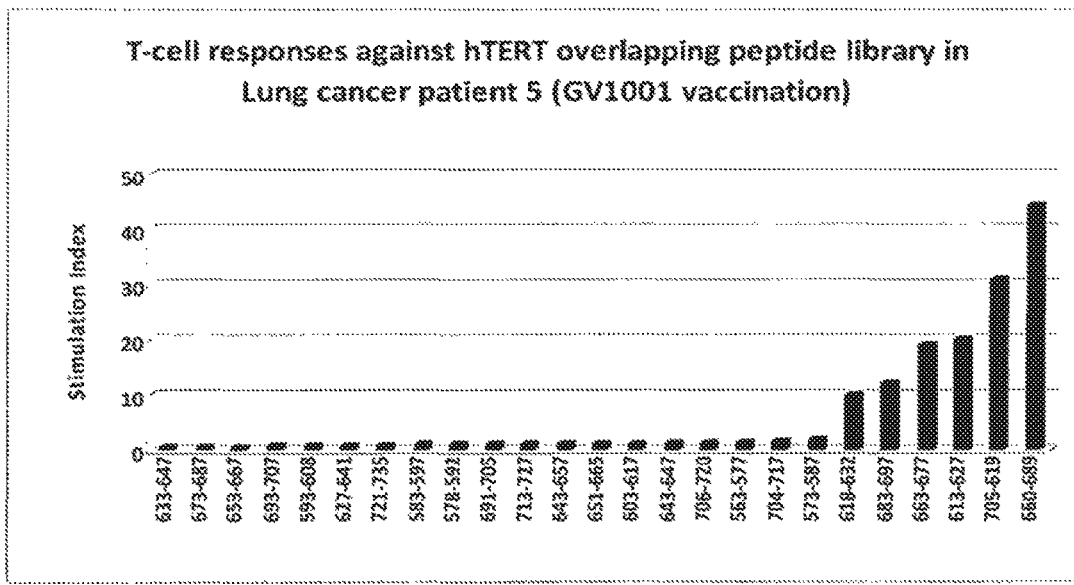
FIG. 8 is a graph showing T-cell response against hTERT overlapping peptide library in a lung cancer patient following vaccination with GV1001 (SEQ. ID NO. 10).
Figure 9:
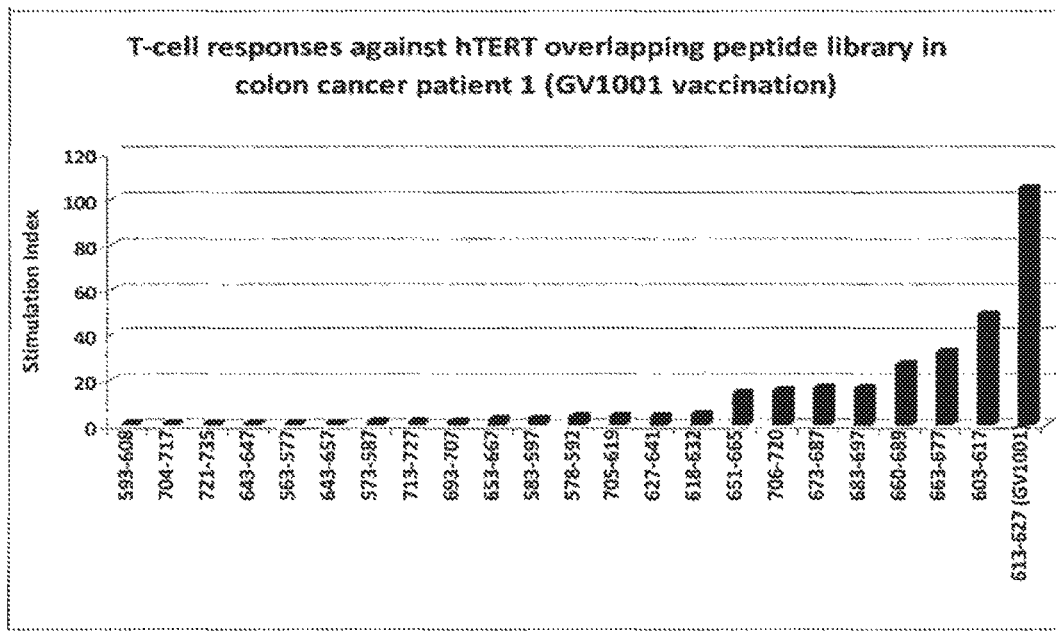
FIG. 9 is a graph showing T-cell response against hTERT overlapping peptide library in a colon cancer patient following vaccination with GV1001 (SEQ. ID NO. 10).
Figure 10:
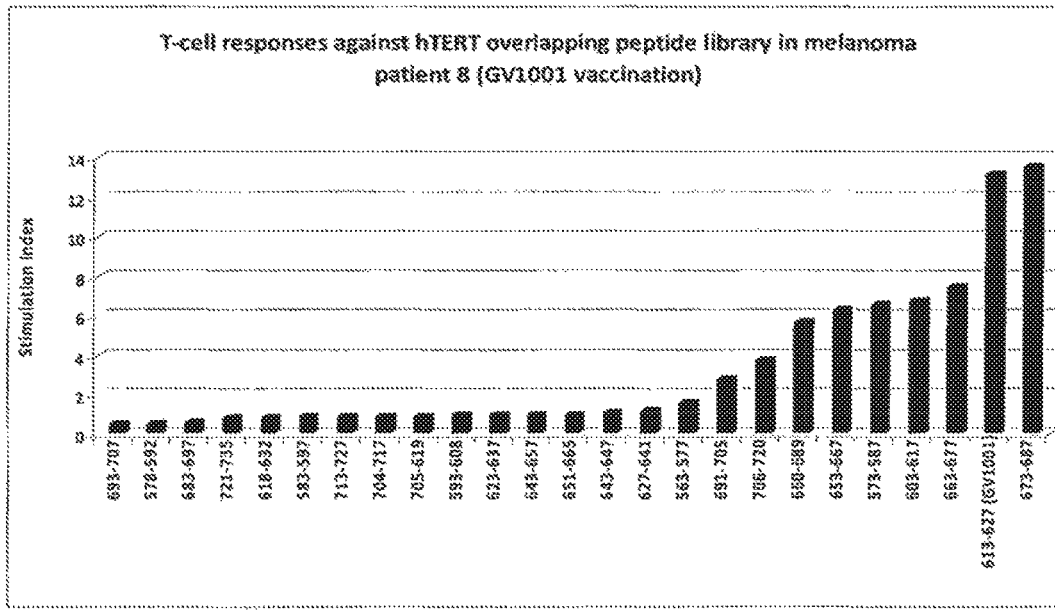
FIG. 10 is a graph showing T-cell response against hTERT overlapping peptide library in a second melanoma patient following vaccination with GV1001 (SEQ. ID NO. 10).
Figure 11:
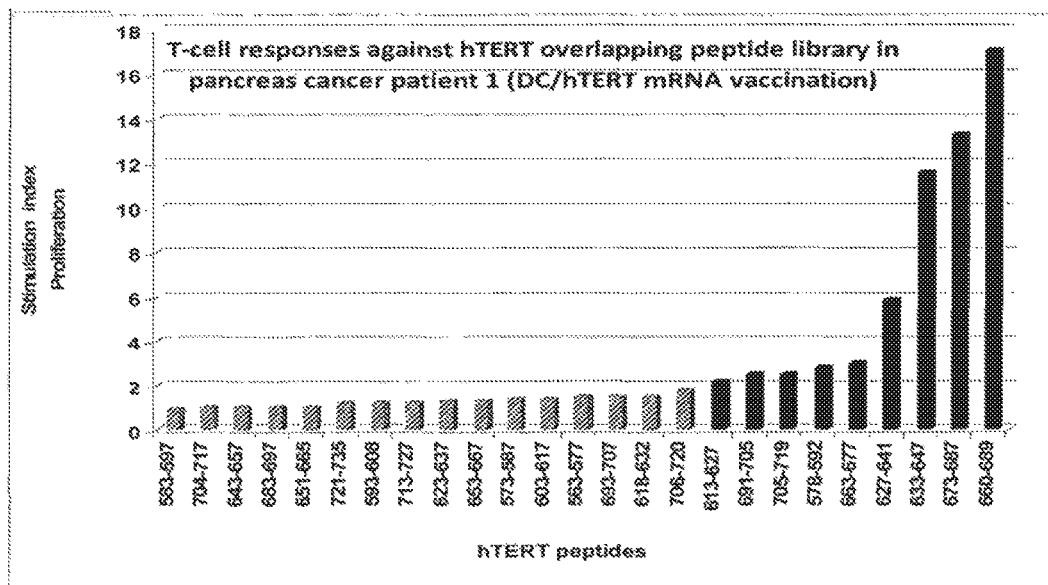
FIG. 11 is a graph showing T-cell response against hTERT overlapping peptide library in a pancreas cancer patient following vaccination with DC transfected with hTERT mRNA. The results shown are for the same patient as in FIG. 1.

The last two patients have not been tested for responses against the 30-mer 660-689 (SEQ. ID NO. 1) as this peptide was synthesized after the tests. The peptide of SEQ. ID NO. 1 gave very strong responses in the GV1001 vaccinated lung cancer patient. 75% of the T-cell clones derived from the culture with this peptide were specific which indicates that this clone is present in the patient at a high frequency. This is the same lung cancer patient whose hTERT-specific CD8+ T cells are shown in the histogram of FIG. 6.

As the patients tested (except the non-vaccinated patient shown) have been selected due to their extraordinary clinical courses, the strong responses detected against the peptides listed in Table 1 indicate that these peptides are clinically relevant epitopes.

TABLE 3

| SEQ. ID NO. | Position in hTERT Amino acid sequence | Peptide sequence | Former Peptide Name | Number of amino acids in peptide sequence |
|---|---|---|---|---|
| 42 | 563-577 | VTETTFQKNRLFFYR | 710 | 15 |
| 43 | 573-587 | LFFYRKSVWSKLQSI | 711 | 15 |
| 44 | 583-597 | KLQSIGIRQHLKRVQ | 712 | 15 |
| 45 | 603-617 | EAEVRQHREARPALL | 713 | 15 |
| 46 | 613-627 | RPALLTSRLRFIPKP | 714 | 15 |
| 47 | 623-637 | FIPKPDGLRPIVNMD | 715 | 15 |
| 48 | 643-657 | RTFRREKRAERLTSR | 717 | 15 |
| 49 | 653-667 | RLTSRVKALFSVLNY | 718 | 15 |
| 2 | 663-677 | SVLNYERARRPGLLG | 719 | 15 |
| 50 | 683-697 | LDDIHRAWRTFVLRV | 721 | 15 |
| 51 | 693-707 | FVLRVRAQDPPPELY | 722 | 15 |
| 5 | 721-735 | PQDRLTEVIASIIKP | 723 | 1 |
| 53 | 578-592 | KSVWSKLQSIGIRQH | 724 | 15 |
| 7 | 691-705 | RTFVLRVRAQDPPPE | 725 | 15 |
| 9 | 651-665 | AERLTSRVKALFSVL | 728 | 15 |
| 4 | 593-608 | LKRVQLRELSEAEVRQ | 731 | 16 |
| 1 | 660-689 | ALFSVLNYERARRPGLLGASVLGLDDIHRA | 719-20 | 30 |
| 3 | 674-683 | GLLGASVLGL | 720GLL | 10 |
| 6 | 653-661 | RLTSRVKAL | 728RLT | 9 |
| 4 | 615-624 | ALLTSRLRFI | 615ALL | 10 |
| 5 | 613-621 | RPALLTSRL | 613RPA | 9 |

Example 5

The sequence of the polypeptide of SEQ. ID NO. 1 (the 30-mer 660-689) was analysed for immunogenic fragments predicted to bind different HLA class I alleles (prediction is performed using the SYFPEITHI database for MHC ligands and peptide motifs). The results are shown in Table 4.

TABLE 4

| SEQ. ID NO. | Peptide Sequence | Peptide Position | No. amino acids | Predicted binding to HLA class I alleles |
|---|---|---|---|---|
| 3 | GLLGASVLGL | 674-683 | 10 | HLA-A*0201, HLA-A*03 |
| 17 | VLGLDDIHRA | 680-689 | 10 | HLA-A*0201, |
| 8 | GASVLGLDDI | 677-686 | 10 | HLA-A*0201, |
| 19 | ALFSVLNYER | 663-672 | 10 | HLA-A*0201, HLA-A*03, HLA-A-*1101 |
| 20 | SVLNYERARR | 663-672 | 10 | HLA-A*03, HLA-A*1101, HLA-A*6801 |
| 21 | SVLGLDDIHR | 679-688 | 10 | HLA-A*03, HLA-A*1101, HLA-A*6801 |
| 22 | FSVLNYERAR | 662-671 | 10 | HLA-A*1101 |
| 23 | NYERARRPGL | 677-675 | 10 | HLA-A*2402 |
| 24 | YERARRPGLL | 667-676 | 10 | HLA-B*4402, HLA-B*18 |
| 25 | RPGLLGASVL | 672-681 | 10 | HLA-B*0702, HLA-B*5101 |
| 26 | ERARRPGLL | 668-676 | 9 | HLA-A*26, HLA-B*1402, HLA-B*2705, HLA-B*2709, HLA-B*08 |
| 27 | VLGLDDIHR | 680-688 | 9 | HLA-A*6801 |
| 28 | SVLNYERAR | 663-671 | 9 | HLA-A*6801, HLA-A*0 |
| 29 | VLNYERARR | 664-672 | 9 | HLA-A*6801, HLA-A*03 |
| 30 | ARRPGLLGA | 670-678 | 9 | HLA-B*1402, HLA_B*4501 |
| 31 | PGLLGASVL | 673-681 | 9 | HLA-B*1402, HLA-B*5101, HLA-B*2705 |
| 12 | LLGASVLGL | 675-683 | 9 | HLA-B*1402 |
| 11 | YERARRPGL | 667-675 | 9 | HLA-B*18, HLA-B*37, HLA-B*4001, HLA_B*4402, HLA-B*4901, HLA-B*08 |
| 32 | RRPGLLGAS | 671-679 | 9 | HLA-B*2705 |
| 33 | ALFSVLNYE | 660-668 | 9 | HLA-A*0201, |
| 34 | GLLGASVLG | 674-682 | 9 | HLA-A*0201, HLA-A*03 |
| 35 | SVLGLDDIH | 679-687 | 9 | HLA-A*03 |
| 36 | ERARRPGL | 668-675 | 8 | HLA-B*1402, HLA-B*08 |
| 37 | ARRPGLLG | 670-677 | 8 | HLA-B*1402 |
| 38 | GLLGASVL | 674-681 | 8 | HLA-B*1402, HLA-B*08 |
| 39 | RARRPGLL | 669-676 | 8 | HLA-B*5101, HLA-B*08 |
| 40 | LGASVLGL | 676-683 | 8 | HLA-B*5101 |

Example 6

A comparison of the patients studied in Example 4 was carried out. In brief, seven patients were identified as clinical responders following a cancer diagnosis and vaccination with an hTERT vaccine. These patients were identified based on a combination of prolonged survival and clinical response. The clinical response could either be stable disease (SD), partial response (PR) or complete response (CR). The vaccinated melanoma patients were diagnosed with stage IV at the time of inclusion in the clinical trial, but had no brain metastases. Lung cancer patient P5 was diagnosed with stage IV, inoperable lung cancer and colon cancer patient P1 with late stage inoperable colon cancer. Lung cancer patient P6 was a stage IV lung cancer patient with a 12-week life expectancy. Pancreas cancer patient P1 had relapsed, inoperable pancreas cancer and a life expectancy of 8-10 months. Four of the patients (designated Melanoma P7-P8, Lung cancer P5 and Colon cancer P1) had each been vaccinated with the peptide GV1001 (SEQ ID NO. 10). The fifth patient (designated Lung cancer P6) and the sixth patient (designated Pancreas cancer 1) had been vaccinated with dendritic cells transfected with mRNA encoding hTERT. The seventh patient, Melanoma patient P9, had not been vaccinated at the time of the study and instead developed a spontaneous response following development of the cancer. (An eighth and final patient was also identified as a clinical responder but samples from this patient were not available for study.)

Figure 14:
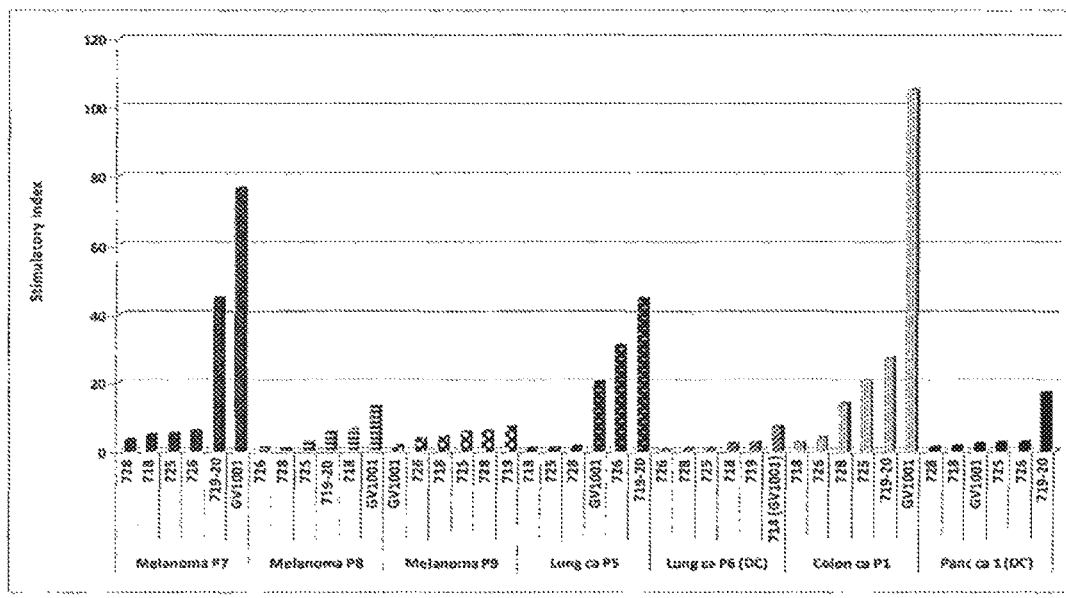
FIG. 14 is a graph showing a summary of the results from FIGS. 7 to 13 for selected hTERT peptides.

The proliferative T-cell responses of each patient to a series of peptides were then determined as explained in Example 1 The results are tabulated in Table 5 and are shown graphically in FIG. 14 in which the peptide designations are referenced in Table 6 (the results for peptides 726 and GV1001 are shown only for comparison).

TABLE 5

| Patient | hTERT peptides | | | | | |
| --- | --- | --- | --- | --- | --- | --- |
| | 718 | 725 | 726 | 728 | 719-20 | GV1001 |
| Melanoma P7 | 4.8 | 4.9 | 5.8 | 3.2 | 44.5 | 76.5 |
| Melanoma P8 | 6.3 | 2.8 | 0.9 | 1 | 5.7 | 13.2 |
| Melanoma P9 | 4.2 | 5.7 | 3.7 | 5.9 | 6.9 | 1.7 |
| Lung ca P5 | 0.8 | 1.1 | 31 | 1.2 | 44.5 | 20.1 |
| Lung ca P6 | 2.1 | 0.8 | 0.6 | 0.7 | 2.5 | 7.1 |
| Colon ca P1 | 2.6 | 20.6 | 4 | 13.9 | 27.2 | 105.1 |
| Pancreas ca P1 | 1.3 | 2.5 | 2.5 | 1 | 17.1 | 2.2 |

TABLE 6

| Former peptide name | SEQ ID NO. |
| --- | --- |
| 719-20 | 1 |
| 725 | 7 |
| 718 | 8 |
| 728 | 9 |
| GV1001 | 10 |

It was observed that all of the patients responded to GV1001 (i.e. they had SI>2). Due to high background caused by auto-MLC in the dendritic cell-vaccinated patients (Lung ca. P7 and Pancreas ca. P1) the SI values are low compared with those found in other patients.

Example 7

Four patients who were clinical non-responders following a lung cancer diagnosis and a GV1001 (SEQ ID NO. 10) peptide vaccination were studied. These patients were all stage IV lung cancer patients vaccinated with GV1001. These patients were randomly selected amongst those patients who had an immune response against GV1001 but still experienced progressive disease and short term survival compared to other patients with an immune response against the vaccine. The proliferative T-cell responses of each patient to a series of peptides were determined in the same manner as in Example 1, at one time point. The peak response of each patient during the study period to peptide GV1001 is also shown which confirms that each patient responded immunologically to GV1001 vaccination.

Figure 15:
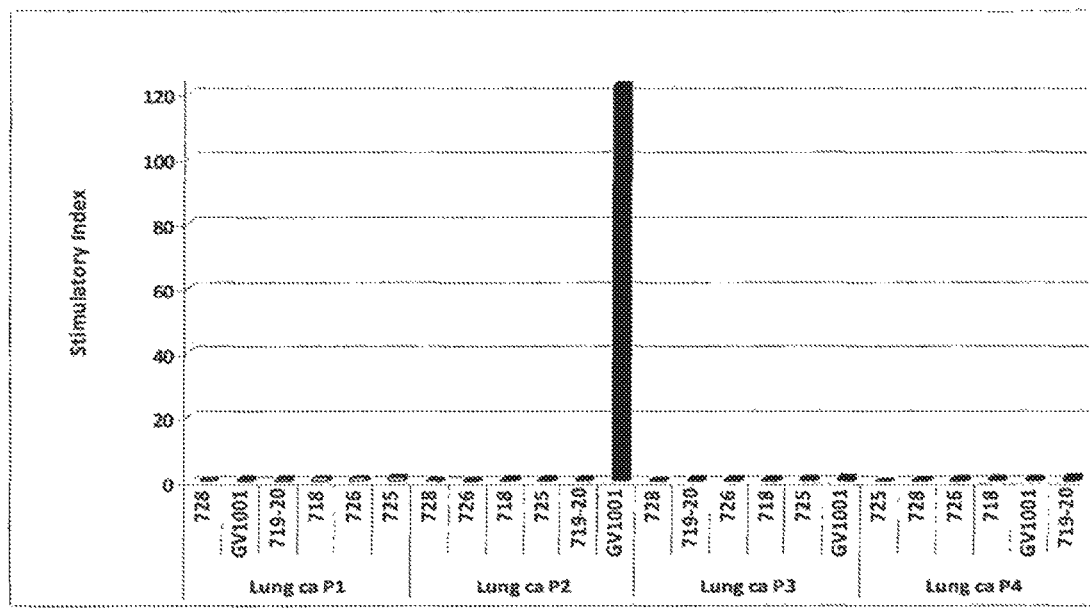
FIG. 15 is a graph showing T-cell responses against selected hTERT peptides in four lung cancer patients.
Figure 10:
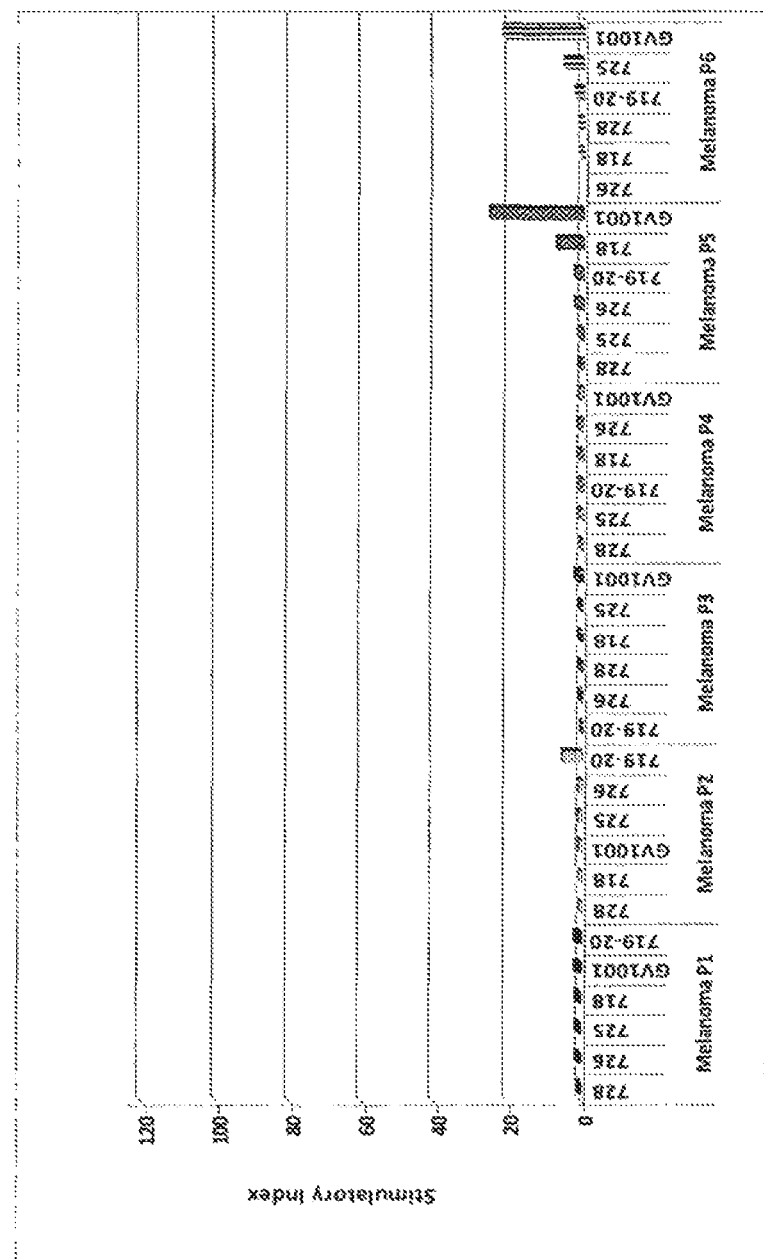

The results are tabulated in Table 7 and are shown graphically in FIG. 15 and the peptide designations are referenced in Table 6.

TABLE 7

| Patient | hTERT peptides | | | | | | Peak response GV1001 |
| --- | --- | --- | --- | --- | --- | --- | --- |
| | 718 | 725 | 726 | 728 | 719-20 | GV1001 | |
| Lung ca P1 | 1.2 | 1.3 | 1.2 | 0.8 | 1 | 0.9 | 60.95 |
| Lung ca P2 | 0.9 | 1 | 0.8 | 0.6 | 1.1 | 122.8 | 122.8 |
| Lung ca P3 | 1.1 | 1.2 | 1.1 | 0.8 | 0.9 | 1.4 | 161.6 |
| Lung ca P4 | 1.1 | 0.4 | 1.1 | 0.7 | 1.5 | 1.2 | 13.3 |

All four of the patients showed very low or no response to the peptides of SEQ ID NOS. 1, 7, 8 and 9.

Example 8

Six patients who were clinical non-responders following a melanoma cancer diagnosis and a GV1001 peptide (SEQ ID NO. 10) vaccination were studied. These patients were all stage IV melanoma patients and included in the same GV1001 vaccination trial as melanoma patients P7 and P8 who were long term survivors (see Example 6). These patients were randomly selected amongst those who showed an immune response against the vaccine, but still experienced only short term survival. Five of the patients also experienced progressive disease and one patient, designated Melanoma P3, experienced some stabilization of the disease but still had short survival. The proliferative T-cell responses of each patient to a series of peptides were determined in the same manner as in Example 1, at one time point. The peak response of each patient during the study period to peptide GV1001 is also shown which confirms that each patient responded immunologically to GV1001 vaccination.

The results are tabulated in Table 8 and shown graphically in FIG. 16 and the peptide designations are referenced in Table 6.

TABLE 8

| Patient | hTERT peptides | | | | | | Peak response GV1001 |
| --- | --- | --- | --- | --- | --- | --- | --- |
| | 718 | 725 | 726 | 728 | 719-20 | GV1001 | |
| Melanoma P1 | 0.9 | 0.9 | 0.9 | 0.8 | 1.6 | 1.4 | 26.0 |
| Melanoma P2 | 0.8 | 1 | 1 | 0.6 | 5.3 | 0.9 | 38.7 |
| Melanoma P3 | 0.6 | 0.7 | 0.5 | 0.5 | 0.3 | 1.8 | 3.7 |
| Melanoma P4 | 1.1 | 1 | 1.2 | 0.8 | 1 | 1.2 | 10.7 |
| Melanoma P5 | 7.1 | 1.2 | 1.9 | 0.9 | 1.9 | 25.2 | 35.4 |
| Melanoma P6 | 0.8 | 4.8 | n.t. | 1.3 | 1.8 | 21.4 | 122.0 |

All six of the patients showed very low or no response to the peptides of SEQ ID NOS. 1, 7, 8 and 9.

Conclusion of Examples 1 to 8

A summary of the patients studied in Examples 1 to 8 is provided in Table 9. All patients responded immunologically to the GV1001 peptide. The patients were classed as either clinical responders or clinical non-responders based on their clinical response which included stable disease (SD), tumour regression (PR or CR) and unexpectedly long survival time. Both clinical responders and clinical non-responders were selected from the same or similar vaccination trials.

TABLE 9

| Patient | Cancer | Vaccine | Vaccine-specific T cell response at time-point tested | Survival (Months) | Clinical response | Clinical Responder |
|---|---|---|---|---|---|---|
| Lung ca P4 | Lung cancer | GV1001 | Yes | 10 | PD | No |
| Lung ca P3 | Lung cancer | GV1001 | Yes | 20 | PD | No |
| Lung ca P1 | Lung cancer | GV1001 | Yes | 14 | PD | No |
| Lung ca P2 | Lung cancer | GV1001 | Yes | 6 | PD | No |
| Melanoma P4 | Melanoma | GV1001 | Yes | 8 | PD | No |
| Melanoma P6 | Melanoma | GV1001 | Yes | 8 | PD | No |
| Melanoma P5 | Melanoma | GV1001 | Yes | 12 | PD | No |
| Melanoma P1 | Melanoma | GV1001 | Yes | 10 | PD | No |
| Melanoma P3 | Melanoma | GV1001 | Yes | 10 | SD | No |
| Melanoma P2 | Melanoma | GV1001 | Yes | 9 | PD | No |
| Melanoma P7 | Melanoma | GV1001 | Yes | 65+ | alive, PR | Yes |
| Melanoma P8 | Melanoma | GV1001 | Yes | 21 | increased TTP, PR | Yes |
| Melanoma P9 | Melanoma | Spontaneous response, non-vaccinated | Yes | 30+ | alive, SD | Yes |
| Lung ca P5 | Lung cancer | GV1001 | Yes | 106+ | alive, CR | Yes |
| Lung ca P6 | Lung cancer | DC/hTERT mRNA | Yes | 16 | PR | Yes |
| Colon ca P1 | Colon cancer | GV1001 | Yes | 80+ | alive, CR | Yes |
| Pancreas ca P1 | Pancreas cancer | DC/hTERT mRNA | Yes | 43+ | alive, CR | Yes |

+signifies that the patient is still alive
PD = Progressive disease
SD = Stable disease
PR = Partial response
CR = Complete response
TTP = time to progression The data presented here strongly indicate that administering any of the peptides of SEQ. ID NOS. 1 to 9 to individuals will induce T-cell responses to the administered peptide in at least some individuals. The presence of T-cell responses to the peptides of SEQ. ID NOS. 1 to 9 in patients to whom other hTERT peptide vaccines or transfected dendritic cells have been administered demonstrates that the peptides of SEQ. ID NOS. 1 to 9 can be bound and presented by patients' MHC molecules and that patients have T cells within their repertoires capable of binding the peptides when presented. Thus when the peptides of SEQ. ID NOS. 1 to 9 are administered to individuals, T-cell responses to the peptides are to be expected.

Moreover, the data provided in Examples 6 to 8 demonstrate that T cell responses against the hTERT peptides of SEQ ID NOS. 1, 7, 8 and 9 described herein are associated with favorable clinical responses in patients with different forms of cancer. In a number of short term survivors who had been treated in the same way by an hTERT vaccine and who had responded to this vaccine, responses to the hTERT peptides of SEQ ID NOS. 1, 7, 8 and 9 were only sporadically observed. It is also notable that in some of these short term survivors, the response to the GV1001 peptide was strong. We interpret these results to mean that response to a single peptide (i.e. GV1001) alone is not sufficient to provide clinical response/long term survival, since in the majority of patients with an immune response to this peptide, survival was short.

Figure 17:
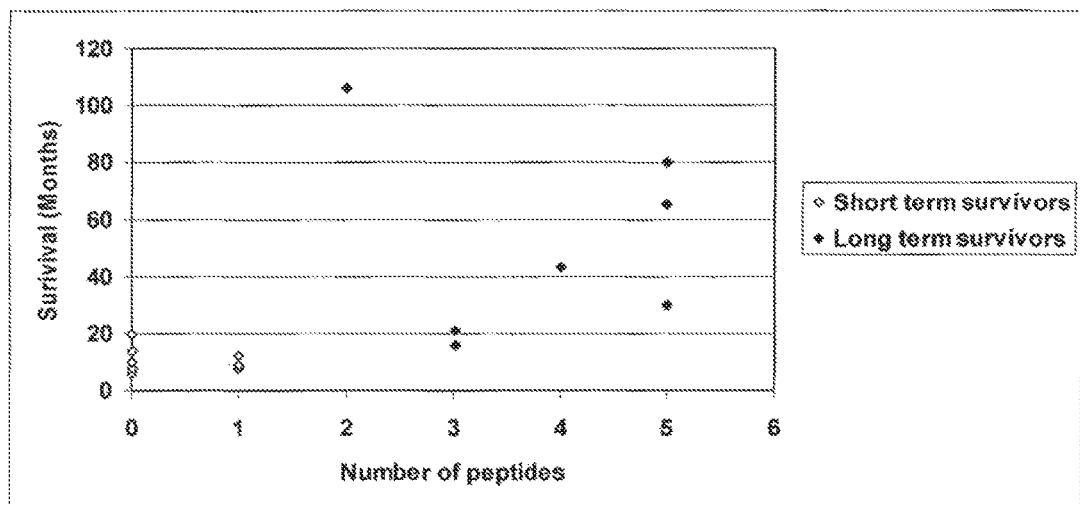
FIG. 17 is a scatter plot showing the number of months' survival for each patient against the number of peptides inducing an immune response.

This is confirmed by the scatter plot analysis shown in FIG. 17 which compares the number of hTERT peptides to which patients demonstrated an immune response with the length of survival of the patients. As can be seen in FIG. 17, there is a clear correlation between longer survival times and immune responses to a greater number of hTERT peptides.

Figure 18:
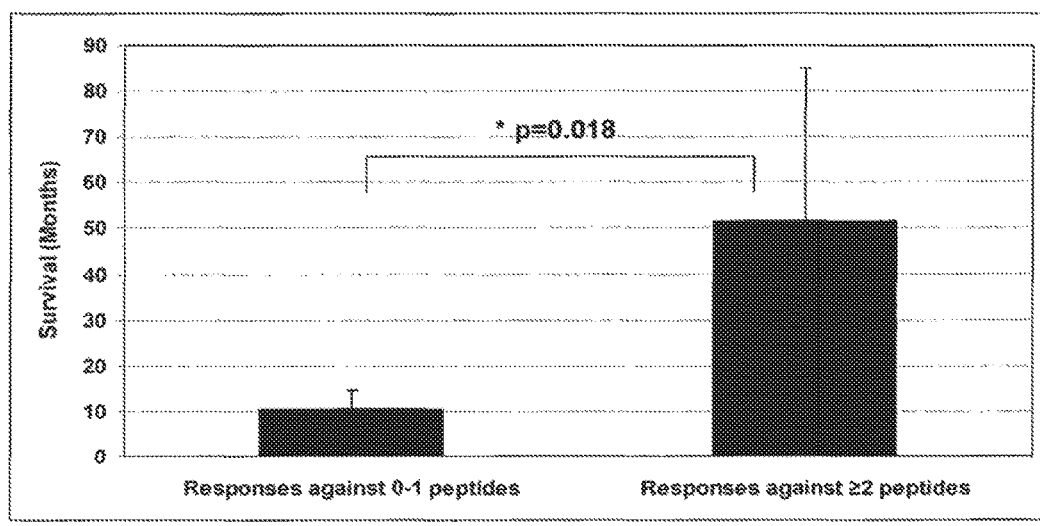
FIG. 18 is a graph showing survival for the different patients tested and split into two groups depending on their immune responses against the peptide sequences against selected hTERT peptides. Those responding against 0-1 peptides in addition to GV1001 were placed in one group and those responding against 2 or more peptides were placed in the other group. Survival was analysed for the two groups using an independent group t-test. A preliminary test for equality of survival indicates that the survival of the two groups is significantly different. Therefore a two-sample t-test was performed that does not assume equal survival. Using the unequal variances t-test, $t(6,1)=-3,22$, $p=0.018$. Statistics were performed using WINKS SDA Software (Texasoft, Cedar Hill, Tex.) Statistical decisions were made at $p=0.05$. For these data, the Mean (SD) survival for the group 0-1 peptides is 10,7(3,9455), N=10, and the Mean (SD) for the group ≥2 peptides is 51,5714(33,3909), N=7.

In addition, the analysis shown in FIG. 18 demonstrates that those patients responding against 2 or more hTERT peptides in addition to GV1001 had an increased length of survival that was statistically significant compared with those patients showing an immune response to 0 or 1 hTERT peptides in addition to GV1001.

Furthermore, the data disclosed herein provide strong evidence pointing to a crucial role for the hTERT peptides of SEQ ID NOS. 1, 7, 8 and 9 in beneficial immune responses. Therefore, active immunization with these novel peptides should induce clinically relevant immune responses in a higher number of patients and thus result in prolonged survival in a higher proportion of patients than is achievable by vaccination with the GV1001 peptide alone.

We demonstrate that responses against the peptides of SEQ ID NOS. 1, 7, 8 and 9 arise naturally after vaccination with unrelated peptides in clinical responders contrary to the patients that do not do well clinically. The mechanism behind this natural immunization is believed to be presentation of these peptides by antigen presenting cells that have engulfed dead tumour cells carrying hTERT and processed the hTERT protein by its proteolytic machinery to yield an array of naturally processed hTERT peptides that correspond to the peptides of SEQ ID NOS. 1, 7, 8 and 9 described herein. The demonstration that many of the same peptides are recognized by T cells taken from patients that have been immunized by hTERT mRNA transfected antigen presenting cells (dendritic cells), and that these patients have done exceptionally well after vaccination, further strengthen this notion. By boosting or inducing these responses through vaccination with a peptide of the present invention or a cocktail of such peptides that have thus already been clinically validated, it will be possible to induce clinical responses and prolonged survival in a much larger proportion of patients.

Example 9

The results from Examples 1 to 8 were also examined for the most efficacious combination of peptides which would thus be suitable to combine to produce a cocktail of peptides. It was observed that the peptides of SEQ. ID NOS: 1, 7 and 9 had complementary effects for the following reasons.

The MHC binding motifs of each of SEQ. ID NOS: 1, 7 and 9 and immunogenic fragments of the sequences are shown in Table 10.

TABLE 10

| Peptide | Sequence | MHC Binding Motif |
|---|---|---|
| SEQ ID NO. 1 | ALFSVLNYERARRPGLLGASVLGLDDIHRA | Th (HLA-DR*01, 04, 07, 15) |
| | SVLNYERARRPGLLG | Th (HLA-DR*01, 04, 07, 15) |
| | FSVLNYERARRPGLL | Th (HLA-DR*01, 04, 07, 15) |
| | ARRPGLLGASVLGLD | Th (HLA-DR*01, 04, 07, 15) |
| | RARRPGLLGASVLGL | Th (HLA-DR*01, 04, 07, 15) |
| | VLNYERARRPGLLGA | Th (HLA-DR*01, 04, 07, 15) |
| | RPGLLGASVLGLDDI | Th (HLA-DR*01, 04, 07, 15) |
| | VLNYERARRPGLLGA | Th (HLA-DR*01, 04, 07, 15) |
| | GLLGASVLGL | CTL (HLA-A2, -B7) |
| | GLLGASVLG | CTL (HLA-A2, -B7) |
| | LLGASVLGL | CTL (HLA-A2, -B7) |
| | ALFSVLNYE | CTL (HLA-A2, -B7) |
| | RPGLLGASVL | CTL (HLA-A2, -B7) |
| | RPGLLGASV | CTL (HLA-A2, -B7) |
| SEQ ID NO. 7 | RTFVLRVRAQDPPPE | Th (HLA-DR*01, 11, 15) |
| | RVRAQDPPPE | CTL (HLA-A3) |
| | FVLRVRAQD | CTL (HLA-A3) |
| SEQ ID NO. 9 | AERLTSRVKALFSVL | Th (HLA-DR*03, 11) |
| | RLTSRVKAL | CTL (HLA-A2, -A3, -B44) |
| | RVKALFSVL | CTL (HLA-A2, -A3, -B44) |
| | AERLTSRVK | CTL (HLA-A2, -A3, -B44) |
| | ERLTSRVKAL | CTL (HLA-A2, -A3, -B44) |

As can be seen from Table 10 the peptides of SEQ. ID NOS: 1, 7 and 9 and their immunogenic fragments are able to bind to a wide range of HLA molecules presenting either Th or CTL epitopes. Therefore, these peptides are able to generate immune responses over a very broad patient population.

In addition, the peptides of SEQ. ID NOS: 1, 7 and 9 have proven immunogenicity across the clinical responder patients reported in Example 6 and relatively greater immunological response in clinical responders than in clinical non-responders.

More specifically, for the peptide of SEQ. ID NO. 1 there were immunological responses in 7/7 clinical responders compared with immunological responses in 1/10 clinical non-responders. Several of the responding long term survivors also showed CTL responses by pentamer analysis.

For the peptide of SEQ ID NO 7 there were immunological responses in 5/7 clinical responders compared with immunological responses in 1/10 clinical non-responders.

For the peptide of SEQ ID NO: 9 there were immunological responses in 3/7 clinical responders compared with immunological responses in 0/10 clinical non-responders in addition to CTL responses shown by pentamer analysis in 3 of the patients, one of them being additional to the 3 showing proliferative responses.

Accordingly, this analysis of the results demonstrates that a cocktail of peptides of SEQ. ID NOS: 1, 7 and 9 is expected to have a high level of efficacy over a broad range of the human population.

REFERENCES

Alldawi L, Takahashi M, Narita M, Ayres F, Tsukada N, Osman Y, Furukawa T, Aizawa Y (2005). Effect of prostaglandin E2, lipopolysaccharide, IFN-gamma and cytokines on the generation and function of fast-DC. *Cytotherapy.* 7(2):195-202.

Aloysius M M, Mc Kechnie A J, Robins R A, Verma C, Eremin J M, Farzaneh F, Habib N A, Bhalla J, Hardwick N R, Satthaporn S, Sreenivasan T, El-Sheemy M, Eremin O. (2009). Generation in vivo of peptide-specific cytotoxic T cells and presence of regulatory T cells during vaccination with hTERT (class I and II) peptide-pulsed DCs. *J Transl Med.* March 19; 7:18.

Beatty G L, Vonderheide R H. (2008) Telomerase as a universal tumor antigen for cancer vaccines. *Expert Rev Vaccines.* September; 7(7):881-7, Bernhardt S L, Gjertsen M K, Trachsel S, Møller M, Eriksen J A, Meo M, Buanes T, Gaudernack G. 2006. Telomerase peptide vaccination of patients with non-resectable pancreatic cancer: A dose escalating phase I/II study. *Br J Cancer,* 95(11):1474-82.

Brunsvig P F, Aamdal S, Gjertsen M K, Kvalheim G, Markowski-Grimsrud C J, Sve I, Dyrhaug M, Trachsel S, Møller M, Eriksen J A, Gaudernack G. 2006.

Telomerase peptide vaccination: a phase I/II study in patients with non-small cell lung cancer. *Cancer Immunol Immunother.* 55(12):1553-64, Carpelan-Holmström M, Nordling 5, Pukkala E, Sankila R, Lüttges J, Klöppel G, Haglund C. (2005). Does anyone survive pancreatic ductal adenocarcinoma? A nationwide study re-evaluating the data of the Finnish Cancer Registry. *Gut.* March; 54(3):385-7.

Darrah P A, Patel D T, De Luca P M, Lindsay R W, Davey D F, Flynn B J, Hoff S T, Andersen P, Reed S G, Morris S L, Roederer M, Seder R A. (2007). Multifunctional TH1 cells define a correlate of vaccine-mediated protection against *Leishmania major. Nat Med.* July; 13(7):843-50.

Domchek S M, Recio A, Mick R, Clark C E, Carpenter E L, Fox K R, DeMichele A, Schuchter L M, Leibowitz M S, Wexler M H, Vance B A, Beatty G L, Veloso E, Feldman M D, Vonderheide R H. 2007. Telomerase-specific T-cell immunity in breast cancer: effect of vaccination on tumor immunosurveillance. *Cancer Res.* 67(21):10546-55.

Ho W Y, Nguyen H N, Wolfl M, Kuball J, Greenberg P D (2006). In vitro methods for generating CD8+ T-cell clones for immunotherapy from the naïve repertoire. *J Immunol Methods.* March 20; 310(1-2):40-52.

Hunder N N, Wallen H, Cao J, Hendricks D W, Reilly J Z, Rodmyre R, Jungbluth A, Gnjatic S, Thompson J A, Yee C. 2008. Treatment of metastatic melanoma with autologous CD4+ T cells against N Y-ESO-1.*N Engl J Med.* 358(25):2698-703.

Kim N W, Piatyszek M A, Prowse K R, Harley C B, West M D, Ho P L, Coviello G M, Wright W E, Weinrich S L, Shay J W. (1994). Specific association of human telomerase activity with immortal cells and cancer. *Science.* December 23; 266(5193):2011-5.

Kyte J A, Mu L, Aamdal S, Kvalheim G, Dueland S, Hauser M, Gullestad H P, Ryder T, Lislerud K, Hammerstad H, Gaudernack G. 2006. Phase I/II trial of melanoma therapy with dendritic cells transfected with autologous tumor-mRNA. *Cancer Gene Ther.* 13(10):905-18.

Liu J P, Chen W, Schwarer A P, Li H. (2009) Telomerase in cancer immunotherapy. Biochim Biophys Acta. September 12; 7

Mu L J, Gaudernack G, Saebøe-Larssen 5, Hammerstad H, Tierens A, Kvalheim G. (2003). A protocol for generation of clinical grade mRNA-transfected monocyte-derived dendritic cells for cancer vaccines. *Scand J Immunol.* November; 58(5):578-86.

Saebøe-Larssen 5, Fossberg E, Gaudernack G. 2002. mRNA-based electrotransfection of human dendritic cells and induction of cytotoxic T lymphocyte responses against the telomerase catalytic subunit (hTERT). *J Immunol Methods.* 259(1-2):191-203.

Schroers R, Huang X F, Hammer J, Zhang J, Chen S Y. 2002. Identification of HLA DR7-restricted epitopes from human telomerase reverse transcriptase recognized by CD4+ T-helper cells. *Cancer Res.* May 1; 62(9):2600-5.

Schroers R, Shen L, Rollins L, Rooney C M, Slawin K, Sonderstrup G, Huang X F, Chen S Y. (2003).

Human telomerase reverse transcriptase-specific T-helper responses induced by promiscuous major histocompatibility complex class II-restricted epitopes. *Clin Cancer Res,* October 15; 9(13):4743-55.

Shay J W. (1997). Telomerase in human development and cancer. *J Cell Physiol.* November; 173(2):266-70.

Su Z, Dannull J, Yang B K, Dahm P, Coleman O, Yancey D, Sichi S, Niedzwiecki D, Boczkowski D, Gilboa E, Vieweg J. 2005. Telomerase mRNA-transfected dendritic cells stimulate antigen-specific CD8+ and CD4+ T cell responses in patients with metastatic prostate cancer. *J Immunol.* 174(6):3798-807.

Tanaka F, Yamaguchi H, Haraguchi N, Mashino K, Ohta M, Inoue H, Mori M. (2006) Efficient induction of specific cytotoxic T lymphocytes to tumor rejection peptide using functional matured 2 day-cultured dendritic cells derived from human monocytes. *Int J Oncol.* November; 29(5): 1263-8.

Therasse P, Arbuck S G, Eisenhauer E A, Wanders J, Kaplan R S, Rubinstein L, Verweii J, Van Glabbeke M, van Oosterom A T, Christian M C, Gwyther S G. (2000). New guidelines to evaluate the response to treatment in solid tumors. European Organization for Research and Treatment of Cancer, National Cancer Institute of the United States, National Cancer Institute of Canada. *J Natl Cancer Inst.* 2000 Feb. 2; 92(3):205-16.

Welters M J, Kenter G G, Piersma S J, Vloon A P, Löwik M J, Berends-van der Meer D M, Drijfhout J W, Valentijn A R, Wafelman A R, Oostendorp J, Fleuren G J, Offringa R, Melief C J, van der Burg S H. Induction of tumor-specific CD4+ and CD8+ T-cell immunity in cervical cancer patients by a human papillomavirus type 16 E6 and E7 long peptides vaccine. *Clin Cancer Res.* 2008 Jan. 1; 14(1):178-87.

Wobser M, Keikavoussi P, Kunzmann V, Weininger M, Andersen M H, Becker J C. (2006) Complete remission of liver metastasis of pancreatic cancer under vaccination with a HLA-A2 restricted peptide derived from the universal tumor antigen survivin. *Cancer Immunol Immunother*. October; 55(10):1294-8.

Wong H H, Lemoine N R. 2008. Biological approaches to therapy of pancreatic cancer. *Pancreatology.* 8(4-5):431-61.

The invention claimed is:

1. A cocktail of nucleic acid molecules comprising at least first and second different nucleic acid molecules wherein the first nucleic acid molecule is a nucleic acid molecule consisting of a nucleotide sequence encoding a polypeptide comprising a sequence selected from the group consisting of:
   i) SEQ ID NO: 1;
   ii) the sequence of an immunogenic fragment of i) comprising at least 20 amino acids;
   iii) the sequence of an immunogenic fragment of i), wherein the immunogenic fragment consists of the sequence of any one of SEQ ID NOS: 18, 24, 36 or 37; and
   iv) a sequence having at least 95% sequence identity to i) or ii), wherein the polypeptide is less than 100 amino acids in length and does not comprise the sequence of SEQ ID NO: 10 or 62; and wherein the second nucleic acid molecule consists of a nucleotide sequence encoding a polypeptide comprising a sequence selected from a group consisting of:
   v) any one of SEQ ID NOS: 2 to 10;
   vi) the sequence of an immunogenic fragment of v) comprising at least eight amino acids; and
   vii) a sequence having at least 80% sequence identity to v) or vi), wherein the second polypeptide is less than 100 amino acids in length.

2. The cocktail of nucleic acid molecules according to claim 1 wherein the at least first and second different nucleic acid molecules comprise a cocktail of nucleic acid molecules selected from the group consisting of:

i) a cocktail of: a first nucleic acid molecule as defined in claim 1; a nucleic acid molecule consisting of a nucleotide sequence encoding a polypeptide comprising the sequence of SEQ ID NO: 7 or a sequence having at least 80% sequence identity thereto or an immunogenic fragment thereof comprising at least eight amino acids; and a nucleic acid molecule consisting of a nucleotide sequence encoding a polypeptide comprising the sequence of SEQ ID NO: 9 or a sequence having at least 80% sequence identity thereto or an immunogenic fragment thereof comprising at least eight amino acids;

ii) a cocktail of: a first nucleic acid molecule as defined in claim 1; a nucleic acid molecule consisting of a nucleotide sequence encoding a polypeptide comprising the sequence of SEQ ID NO: 8 or a sequence having at least 80% sequence identity thereto or an immunogenic fragment thereof comprising at least eight amino acids; and a nucleic acid molecule consisting of a nucleotide sequence encoding a polypeptide comprising the sequence of SEQ ID NO: 9 or a sequence having at least 80% sequence identity thereto or an immunogenic fragment thereof comprising at least eight amino acids; and iii) a cocktail of: a first nucleic acid molecule as defined in claim 1; a nucleic acid molecule consisting of a nucleotide sequence encoding a polypeptide comprising the sequence of SEQ ID NO: 8 or a sequence having at least 80% sequence identity thereto or an immunogenic fragment thereof comprising at least eight amino acids; and a nucleic acid molecule consisting of a nucleotide sequence encoding a polypeptide comprising the sequence of SEQ ID NO: 10 or a sequence having at least 80% sequence identity thereto or an immunogenic fragment thereof comprising at least eight amino acids, wherein each polypeptide is less than 100 amino acids in length.

3. The cocktail of nucleic acid molecules according to claim 1, part vi), wherein the or each immunogenic fragment encoded by the second nucleotide sequence has the sequence of any one of SEQ ID NOS: 19, 20, 22 to 26, 2.8 to 31, 33, 34, or 36 to 40.

4. A method of eliciting an immune response in a patient with cancer or in an individual prior to any symptoms of cancer, comprising administering the cocktail of nucleic acid molecules according to claim 1 to the patient or the individual.

5. The method according to claim 4, wherein the cancer is selected from breast cancer, prostate cancer, pancreatic cancer, colorectal cancer, lung cancer, malignant melanoma, a leukemia, a lymphoma, ovarian cancer, cervical cancer, or a biliary tract carcinoma.

6. A pharmaceutical composition comprising the cocktail of nucleic acid molecules according to claim 1 and a pharmaceutically acceptable adjuvant, diluent or excipient.

7. The pharmaceutical composition according to claim 6, wherein the pharmaceutical composition comprises a further therapeutic ingredient.

8. The pharmaceutical composition according to claim 6, wherein the cocktail of nucleic acid molecules is present in a dose of between 1 and 500 μg.

9. The pharmaceutical composition according to claim 6, wherein at least one nucleic acid molecule in the cocktail of nucleic acid molecules is coupled to an immunogenic carrier.

10. A method of eliciting an immune response in a patient with cancer or in an individual prior to any symptoms of cancer, comprising administering the pharmaceutical composition according to claim 6 to the patient or the individual.

11. The method according to claim 10, wherein the cancer is selected from breast cancer, prostate cancer, pancreatic cancer, colorectal cancer, lung cancer, malignant melanoma, a leukemia, a lymphoma, ovarian cancer, cervical cancer, or a biliary tract carcinoma.

12. A cocktail of nucleic acid molecules comprising at least two different nucleic acid molecules, wherein the at least two different nucleic acid molecules comprise a cocktail of:

a nucleic acid molecule consisting of a nucleic acid sequence encoding a polypeptide comprising the sequence of SEQ ID NO. 1 or a sequence having at least 80% sequence identity thereto or an immunogenic fragment thereof comprising at least eight amino acids; a nucleic acid molecule consisting of a nucleic acid sequence encoding a polypeptide comprising the sequence of SEQ ID NO. 7 or a sequence having at least 80% sequence identity thereto or an immunogenic fragment thereof comprising at least eight amino acids; and a nucleic acid molecule consisting of a nucleic acid sequence encoding a polypeptide comprising a sequence of SEQ ID NO. 9 or a sequence having at least 80% sequence identity thereto or an immunogenic fragment thereof comprising at least eight amino acids, wherein each polypeptide is less than 100 amino acids in length.

13. The cocktail of nucleic acid molecules according to claim 12, wherein the or each immunogenic fragment encoded by the nucleotide sequence has the sequence of any one of SEQ ID NOS: 17 to 40.

14. A method of eliciting an immune response in a patient with cancer or in an individual prior to any symptoms of cancer, comprising administering the cocktail of nucleic acid molecules according to claim 12 to the patient or the individual.

15. The method according to claim 14, wherein the cancer is selected from breast cancer, prostate cancer, pancreatic cancer, colorectal cancer, lung cancer, malignant melanoma, a leukemia, a lymphoma, ovarian cancer, cervical cancer, or a biliary tract carcinoma.

16. A pharmaceutical composition comprising the cocktail of nucleic acid molecules according to claim 12 and a pharmaceutically acceptable adjuvant, diluent or excipient.

17. The pharmaceutical composition according to claim 16, wherein the pharmaceutical composition comprises a further therapeutic ingredient.

18. The pharmaceutical composition according to claim 16, wherein the cocktail of nucleic acid molecules is present in a dose of between 1 and 500 μg.

19. The pharmaceutical composition according to claim 16, wherein at least one nucleic acid molecule in the cocktail of nucleic acid molecules is coupled to an immunogenic carrier.

20. A method of eliciting an immune response in a patient with cancer or in an individual prior to any symptoms of cancer, comprising administering the pharmaceutical composition according to claim 16 to the patient or the individual.

21. The method according to claim 20, wherein the cancer is selected from breast cancer, prostate cancer, pancreatic cancer, colorectal cancer, lung cancer, malignant melanoma, a leukemia, a lymphoma, ovarian cancer, cervical cancer, or a biliary tract carcinoma.

22. A pharmaceutical composition comprising a nucleic acid molecule consisting of a nucleotide sequence encoding a polypeptide comprising a sequence selected from the group consisting of:
  i) SEQ. ID NO: 1;
  ii) the sequence of an immunogenic fragment of i) comprising at least 24 amino acids;
  iii) the sequence of an immunogenic fragment of i), wherein the immunogenic fragment consists of the sequence of SEQ ID NO: 18, and
  iv) a sequence having at least 95% sequence identity to i) or ii),
wherein the polypeptide is less than 100 amino acids in length and does not comprise the sequence of SEQ ID NO: 10 or 62, and
wherein the pharmaceutical composition comprises a pharmaceutically acceptable adjuvant, diluent or excipient,
wherein the pharmaceutical composition further comprises a therapeutic ingredient, or an immunogenic carrier.

23. A pharmaceutical composition comprising a nucleic acid molecule consisting of a nucleotide sequence encoding a polypeptide comprising a sequence selected from the group consisting of:
  i) SEQ ID NO: 1;
  ii) the sequence of an immunogenic fragment of comprising at least 24 amino acids;
  iii) the sequence of an immunogenic fragment of i), wherein the immunogenic fragment consists of the sequence of SEQ ID NO: 18 and
  iv) a sequence having at least 95% sequence identity to i) or ii),
wherein the polypeptide is less than 100 amino acids in length and does not comprise the sequence of SEQ ID NO: 10 or 62;
wherein the pharmaceutical composition comprises a pharmaceutically acceptable adjuvant, diluent or excipient; and
wherein the nucleic acid molecule is coupled to an immunogenic carrier.

24. A pharmaceutical composition comprising a nucleic acid molecule consisting of a nucleotide sequence encoding a polypeptide comprising a sequence selected from the group consisting of:
  i) SEQ ID NO: 1;
    ii) the sequence of an immunogenic fragment of i) comprising at least 24 amino acids;
  iii) the sequence of an immunogenic fragment of i), wherein the immunogenic fragment consists of the sequence of SEQ ID NO: 18; and
  iv) a sequence having at least 95% sequence identity to i) or ii),
wherein the polypeptide is less than 100 amino acids in length and does not comprise the sequence of SEQ ID NO: 10 or 62,
wherein the pharmaceutical composition comprises a pharmaceutically acceptable adjuvant, diluent or excipient; and wherein the adjuvant is selected from the group consisting of Freund's complete adjuvant, Freund's incomplete adjuvant, aluminium phosphate, aluminium hydroxide, alum, cholera toxin, salmonella toxin and Granulocyte Macrophage-Colony Stimulating Factor.

25. A method of eliciting an immune response in a patient with cancer or in an individual prior to any symptoms of cancer, comprising administering a pharmaceutical composition comprising a nucleic acid molecule consisting of a nucleotide sequence encoding a polypeptide comprising a sequence selected from the group consisting of:
  i) SEQ. ID NO: 1;
  ii) the sequence of an immunogenic fragment of i) comprising at least 24 amino acids;
  iii) the sequence of an immunogenic fragment of i), wherein the immunogenic fragment consists of the sequence of SEQ ID NO: 18; and
  iv) a sequence having at least 95% sequence identity to i) or ii),
wherein the polypeptide is less than 100 amino acids in length and does not comprise the sequence of SEQ ID NO: 10 or 62, and
wherein the pharmaceutical composition comprises a pharmaceutically acceptable adjuvant diluent or excipient;
to the patient or the individual.

26. The method according to claim 25, wherein the cancer is selected from breast cancer, prostate cancer, pancreatic cancer, colorectal cancer, lung cancer, malignant melanoma, a leukemia, a lymphoma, ovarian cancer, cervical cancer, or a biliary tract carcinoma.

27. A vector comprising a nucleic acid molecule consisting of a nucleotide sequence encoding a polypeptide comprising a sequence selected from the group consisting of:
  i) SEQ ID NO: 1;
  ii) the sequence of an immunogenic fragment of i) comprising at least 20 amino acids:
  iii) the sequence of an immunogenic fragment of i), wherein the immunogenic fragment consists of the sequence of any one of SEQ ID NOS: 18, 24, 36 or 37; and
  iv) a sequence having at least 95% sequence identity to i) or ii),
wherein the polypeptide is less than 100 amino acids in length and does not comprise the sequence of SEQ ID NO: 10 or 62.

28. An isolated host cell comprising the vector of claim 27.

29. An isolated antigen presenting cell transfected with a nucleic acid molecule consisting of a nucleotide sequence encoding a polypeptide comprising a sequence selected from the group consisting of:
  i) SEQ ID NO: 1;
  the sequence of an immunogenic fragment of i) comprising at least 20 amino acids;
  iii) the sequence of an immunogenic fragment of i), wherein the immunogenic fragment consists of the sequence of any one of SEQ ID NOS: 18, 24, 36 or 37; and
  iv) a sequence having at least 95% sequence identity to or ii),
wherein the polypeptide is less than 100 amino acids in length and does not comprise the sequence of SEQ ID NO: 10 or 62.

30. The isolated antigen presenting cell of claim 29 wherein the antigen presenting cell is a dendritic cell.

* * * * *

```
                          SEQUENCE LISTING

<160> NUMBER OF SEQ ID NOS: 62

<210> SEQ ID NO 1
<211> LENGTH: 30
<212> TYPE: PRT
<213> ORGANISM: Homo sapiens

<400> SEQUENCE: 1

Ala Leu Phe Ser Val Leu Asn Tyr Glu Arg Ala Arg Arg Pro Gly Leu
1               5                   10                  15

Leu Gly Ala Ser Val Leu Gly Leu Asp Asp Ile His Arg Ala
            20                  25                  30

<210> SEQ ID NO 2
<211> LENGTH: 15
<212> TYPE: PRT
<213> ORGANISM: Homo sapiens

<400> SEQUENCE: 2

Ser Val Leu Asn Tyr Glu Arg Ala Arg Arg Pro Gly Leu Leu Gly
1               5                   10                  15

<210> SEQ ID NO 3
<211> LENGTH: 10
<212> TYPE: PRT
<213> ORGANISM: Homo sapiens

<400> SEQUENCE: 3

Gly Leu Leu Gly Ala Ser Val Leu Gly Leu
1               5                   10

<210> SEQ ID NO 4
<211> LENGTH: 10
<212> TYPE: PRT
<213> ORGANISM: Homo sapiens

<400> SEQUENCE: 4

Ala Leu Leu Thr Ser Arg Leu Arg Phe Ile
1               5                   10

<210> SEQ ID NO 5
<211> LENGTH: 9
<212> TYPE: PRT
<213> ORGANISM: Homo sapiens

<400> SEQUENCE: 5

Arg Pro Ala Leu Leu Thr Ser Arg Leu
1               5

<210> SEQ ID NO 6
<211> LENGTH: 9
<212> TYPE: PRT
<213> ORGANISM: Homo sapiens

<400> SEQUENCE: 6

Arg Leu Thr Ser Arg Val Lys Ala Leu
1               5

<210> SEQ ID NO 7
<211> LENGTH: 15
```

```
<212> TYPE: PRT
<213> ORGANISM: Homo sapiens

<400> SEQUENCE: 7

Arg Thr Phe Val Leu Arg Val Arg Ala Gln Asp Pro Pro Pro Glu
1               5                   10                  15

<210> SEQ ID NO 8
<211> LENGTH: 15
<212> TYPE: PRT
<213> ORGANISM: Homo sapiens

<400> SEQUENCE: 8

Arg Leu Thr Ser Arg Val Lys Ala Leu Phe Ser Val Leu Asn Tyr
1               5                   10                  15

<210> SEQ ID NO 9
<211> LENGTH: 15
<212> TYPE: PRT
<213> ORGANISM: Homo sapiens

<400> SEQUENCE: 9

Ala Glu Arg Leu Thr Ser Arg Val Lys Ala Leu Phe Ser Val Leu
1               5                   10                  15

<210> SEQ ID NO 10
<211> LENGTH: 16
<212> TYPE: PRT
<213> ORGANISM: Homo sapiens

<400> SEQUENCE: 10

Glu Ala Arg Pro Ala Leu Leu Thr Ser Arg Leu Arg Phe Ile Pro Lys
1               5                   10                  15

<210> SEQ ID NO 11
<211> LENGTH: 9
<212> TYPE: PRT
<213> ORGANISM: Homo sapiens

<400> SEQUENCE: 11

Tyr Glu Arg Ala Arg Arg Pro Gly Leu
1               5

<210> SEQ ID NO 12
<211> LENGTH: 9
<212> TYPE: PRT
<213> ORGANISM: Homo sapiens

<400> SEQUENCE: 12

Leu Leu Gly Ala Ser Val Leu Gly Leu
1               5

<210> SEQ ID NO 13
<211> LENGTH: 9
<212> TYPE: PRT
<213> ORGANISM: Homo sapiens

<400> SEQUENCE: 13

Ala Leu Leu Thr Ser Arg Leu Arg Phe
1               5

<210> SEQ ID NO 14
<211> LENGTH: 9
<212> TYPE: PRT
```

-continued

```
<400> SEQUENCE: 14

Leu Leu Thr Ser Arg Leu Arg Phe Ile
1               5

<210> SEQ ID NO 15
<211> LENGTH: 9
<212> TYPE: PRT
<213> ORGANISM: Homo sapiens

<400> SEQUENCE: 15

Arg Val Lys Ala Leu Phe Ser Val Leu
1               5

<210> SEQ ID NO 16
<211> LENGTH: 9
<212> TYPE: PRT
<213> ORGANISM: Homo sapiens

<400> SEQUENCE: 16

Lys Ala Leu Phe Ser Val Leu Asn Tyr
1               5

<210> SEQ ID NO 17
<211> LENGTH: 10
<212> TYPE: PRT
<213> ORGANISM: Homo sapiens

<400> SEQUENCE: 17

Val Leu Gly Leu Asp Asp Ile His Arg Ala
1               5                   10

<210> SEQ ID NO 18
<211> LENGTH: 10
<212> TYPE: PRT
<213> ORGANISM: Homo sapiens

<400> SEQUENCE: 18

Gly Ala Ser Val Leu Gly Leu Asp Asp Ile
1               5                   10

<210> SEQ ID NO 19
<211> LENGTH: 10
<212> TYPE: PRT
<213> ORGANISM: Homo sapiens

<400> SEQUENCE: 19

Ala Leu Phe Ser Val Leu Asn Tyr Glu Arg
1               5                   10

<210> SEQ ID NO 20
<211> LENGTH: 10
<212> TYPE: PRT
<213> ORGANISM: Homo sapiens

<400> SEQUENCE: 20

Ser Val Leu Asn Tyr Glu Arg Ala Arg Arg
1               5                   10

<210> SEQ ID NO 21
<211> LENGTH: 10
<212> TYPE: PRT
<213> ORGANISM: Homo sapiens

<400> SEQUENCE: 21
```

Ser Val Leu Gly Leu Asp Asp Ile His Arg
1               5                   10

<210> SEQ ID NO 22
<211> LENGTH: 10
<212> TYPE: PRT
<213> ORGANISM: Homo sapiens

<400> SEQUENCE: 22

Phe Ser Val Leu Asn Tyr Glu Arg Ala Arg
1               5                   10

<210> SEQ ID NO 23
<211> LENGTH: 10
<212> TYPE: PRT
<213> ORGANISM: Homo sapiens

<400> SEQUENCE: 23

Asn Tyr Glu Arg Ala Arg Arg Pro Gly Leu
1               5                   10

<210> SEQ ID NO 24
<211> LENGTH: 10
<212> TYPE: PRT
<213> ORGANISM: Homo sapiens

<400> SEQUENCE: 24

Tyr Glu Arg Ala Arg Arg Pro Gly Leu Leu
1               5                   10

<210> SEQ ID NO 25
<211> LENGTH: 10
<212> TYPE: PRT
<213> ORGANISM: Homo sapiens

<400> SEQUENCE: 25

Arg Pro Gly Leu Leu Gly Ala Ser Val Leu
1               5                   10

<210> SEQ ID NO 26
<211> LENGTH: 9
<212> TYPE: PRT
<213> ORGANISM: Homo sapiens

<400> SEQUENCE: 26

Glu Arg Ala Arg Arg Pro Gly Leu Leu
1               5

<210> SEQ ID NO 27
<211> LENGTH: 9
<212> TYPE: PRT
<213> ORGANISM: Homo sapiens

<400> SEQUENCE: 27

Val Leu Gly Leu Asp Asp Ile His Arg
1               5

<210> SEQ ID NO 28
<211> LENGTH: 9
<212> TYPE: PRT
<213> ORGANISM: Homo sapiens

<400> SEQUENCE: 28

Ser Val Leu Asn Tyr Glu Arg Ala Arg

```
<210> SEQ ID NO 29
<211> LENGTH: 9
<212> TYPE: PRT
<213> ORGANISM: Homo sapiens

<400> SEQUENCE: 29

Val Leu Asn Tyr Glu Arg Ala Arg Arg
1               5

<210> SEQ ID NO 30
<211> LENGTH: 9
<212> TYPE: PRT
<213> ORGANISM: Homo sapiens

<400> SEQUENCE: 30

Ala Arg Arg Pro Gly Leu Leu Gly Ala
1               5

<210> SEQ ID NO 31
<211> LENGTH: 9
<212> TYPE: PRT
<213> ORGANISM: Homo sapiens

<400> SEQUENCE: 31

Pro Gly Leu Leu Gly Ala Ser Val Leu
1               5

<210> SEQ ID NO 32
<211> LENGTH: 9
<212> TYPE: PRT
<213> ORGANISM: Homo sapiens

<400> SEQUENCE: 32

Arg Arg Pro Gly Leu Leu Gly Ala Ser
1               5

<210> SEQ ID NO 33
<211> LENGTH: 9
<212> TYPE: PRT
<213> ORGANISM: Homo sapiens

<400> SEQUENCE: 33

Ala Leu Phe Ser Val Leu Asn Tyr Glu
1               5

<210> SEQ ID NO 34
<211> LENGTH: 9
<212> TYPE: PRT
<213> ORGANISM: Homo sapiens

<400> SEQUENCE: 34

Gly Leu Leu Gly Ala Ser Val Leu Gly
1               5

<210> SEQ ID NO 35
<211> LENGTH: 9
<212> TYPE: PRT
<213> ORGANISM: Homo sapiens

<400> SEQUENCE: 35

Ser Val Leu Gly Leu Asp Asp Ile His
1               5
```

```
<210> SEQ ID NO 36
<211> LENGTH: 8
<212> TYPE: PRT
<213> ORGANISM: Homo sapiens

<400> SEQUENCE: 36

Glu Arg Ala Arg Arg Pro Gly Leu
1               5

<210> SEQ ID NO 37
<211> LENGTH: 8
<212> TYPE: PRT
<213> ORGANISM: Homo sapiens

<400> SEQUENCE: 37

Ala Arg Arg Pro Gly Leu Leu Gly
1               5

<210> SEQ ID NO 38
<211> LENGTH: 8
<212> TYPE: PRT
<213> ORGANISM: Homo sapiens

<400> SEQUENCE: 38

Gly Leu Leu Gly Ala Ser Val Leu
1               5

<210> SEQ ID NO 39
<211> LENGTH: 8
<212> TYPE: PRT
<213> ORGANISM: Homo sapiens

<400> SEQUENCE: 39

Arg Ala Arg Arg Pro Gly Leu Leu
1               5

<210> SEQ ID NO 40
<211> LENGTH: 8
<212> TYPE: PRT
<213> ORGANISM: Homo sapiens

<400> SEQUENCE: 40

Leu Gly Ala Ser Val Leu Gly Leu
1               5

<210> SEQ ID NO 41
<211> LENGTH: 9
<212> TYPE: PRT
<213> ORGANISM: Homo sapiens

<400> SEQUENCE: 41

Ser Leu Tyr Asn Thr Val Ala Thr Leu
1               5

<210> SEQ ID NO 42
<211> LENGTH: 15
<212> TYPE: PRT
<213> ORGANISM: Homo sapiens

<400> SEQUENCE: 42

Val Thr Glu Thr Thr Phe Gln Lys Asn Arg Leu Phe Phe Tyr Arg
1               5                   10                  15

<210> SEQ ID NO 43
```

```
<211> LENGTH: 15
<212> TYPE: PRT
<213> ORGANISM: Homo sapiens

<400> SEQUENCE: 43

Leu Phe Phe Tyr Arg Lys Ser Val Trp Ser Lys Leu Gln Ser Ile
1               5                   10                  15

<210> SEQ ID NO 44
<211> LENGTH: 15
<212> TYPE: PRT
<213> ORGANISM: Homo sapiens

<400> SEQUENCE: 44

Lys Leu Gln Ser Ile Gly Ile Arg Gln His Leu Lys Arg Val Gln
1               5                   10                  15

<210> SEQ ID NO 45
<211> LENGTH: 15
<212> TYPE: PRT
<213> ORGANISM: Homo sapiens

<400> SEQUENCE: 45

Glu Ala Glu Val Arg Gln His Arg Glu Ala Arg Pro Ala Leu Leu
1               5                   10                  15

<210> SEQ ID NO 46
<211> LENGTH: 15
<212> TYPE: PRT
<213> ORGANISM: Homo sapiens

<400> SEQUENCE: 46

Arg Pro Ala Leu Leu Thr Ser Arg Leu Arg Phe Ile Pro Lys Pro
1               5                   10                  15

<210> SEQ ID NO 47
<211> LENGTH: 15
<212> TYPE: PRT
<213> ORGANISM: Homo sapiens

<400> SEQUENCE: 47

Phe Ile Pro Lys Pro Asp Gly Leu Arg Pro Ile Val Asn Met Asp
1               5                   10                  15

<210> SEQ ID NO 48
<211> LENGTH: 15
<212> TYPE: PRT
<213> ORGANISM: Homo sapiens

<400> SEQUENCE: 48

Arg Thr Phe Arg Arg Glu Lys Arg Ala Glu Arg Leu Thr Ser Arg
1               5                   10                  15

<210> SEQ ID NO 49
<211> LENGTH: 15
<212> TYPE: PRT
<213> ORGANISM: Homo sapiens

<400> SEQUENCE: 49

Arg Leu Thr Ser Arg Val Lys Ala Leu Phe Ser Val Leu Asn Tyr
1               5                   10                  15

<210> SEQ ID NO 50
<211> LENGTH: 15
<212> TYPE: PRT
```

<213> ORGANISM: Homo sapiens

<400> SEQUENCE: 50

Leu Asp Asp Ile His Arg Ala Trp Arg Thr Phe Val Leu Arg Val
1               5                   10                  15

<210> SEQ ID NO 51
<211> LENGTH: 15
<212> TYPE: PRT
<213> ORGANISM: Homo sapiens

<400> SEQUENCE: 51

Phe Val Leu Arg Val Arg Ala Gln Asp Pro Pro Glu Leu Tyr
1               5                   10                  15

<210> SEQ ID NO 52
<211> LENGTH: 15
<212> TYPE: PRT
<213> ORGANISM: Homo sapiens

<400> SEQUENCE: 52

Pro Gln Asp Arg Leu Thr Glu Val Ile Ala Ser Ile Ile Lys Pro
1               5                   10                  15

<210> SEQ ID NO 53
<211> LENGTH: 15
<212> TYPE: PRT
<213> ORGANISM: Homo sapiens

<400> SEQUENCE: 53

Lys Ser Val Trp Ser Lys Leu Gln Ser Ile Gly Ile Arg Gln His
1               5                   10                  15

<210> SEQ ID NO 54
<211> LENGTH: 16
<212> TYPE: PRT
<213> ORGANISM: Homo sapiens

<400> SEQUENCE: 54

Leu Lys Arg Val Gln Leu Arg Glu Leu Ser Glu Ala Glu Val Arg Gln
1               5                   10                  15

<210> SEQ ID NO 55
<211> LENGTH: 15
<212> TYPE: PRT
<213> ORGANISM: Homo sapiens

<400> SEQUENCE: 55

Pro Gly Leu Leu Gly Ala Ser Val Leu Gly Leu Asp Asp Ile His
1               5                   10                  15

<210> SEQ ID NO 56
<211> LENGTH: 15
<212> TYPE: PRT
<213> ORGANISM: Homo sapiens

<400> SEQUENCE: 56

Arg Pro Gly Leu Leu Gly Ala Ser Val Leu Gly Leu Asp Asp Ile
1               5                   10                  15

<210> SEQ ID NO 57
<211> LENGTH: 15
<212> TYPE: PRT

```
<400> SEQUENCE: 57

Val Lys Ala Leu Phe Ser Val Leu Asn Tyr Glu Arg Ala Arg Arg
1               5                   10                  15

<210> SEQ ID NO 58
<211> LENGTH: 15
<212> TYPE: PRT
<213> ORGANISM: Homo sapiens

<400> SEQUENCE: 58

Leu Phe Ser Val Leu Asn Tyr Glu Arg Ala Arg Arg Pro Gly Leu
1               5                   10                  15

<210> SEQ ID NO 59
<211> LENGTH: 15
<212> TYPE: PRT
<213> ORGANISM: Homo sapiens

<400> SEQUENCE: 59

His Arg Ala Trp Arg Thr Phe Val Leu Arg Val Arg Ala Gln Asp
1               5                   10                  15

<210> SEQ ID NO 60
<211> LENGTH: 15
<212> TYPE: PRT
<213> ORGANISM: Homo sapiens

<400> SEQUENCE: 60

Trp Arg Thr Phe Val Leu Arg Val Arg Ala Gln Asp Pro Pro Pro
1               5                   10                  15

<210> SEQ ID NO 61
<211> LENGTH: 15
<212> TYPE: PRT
<213> ORGANISM: Homo sapiens

<400> SEQUENCE: 61

Val Leu Arg Val Arg Ala Gln Asp Pro Pro Pro Glu Leu Tyr Phe
1               5                   10                  15

<210> SEQ ID NO 62
<211> LENGTH: 9
<212> TYPE: PRT
<213> ORGANISM: Homo sapiens

<400> SEQUENCE: 62

Arg Ala Gln Asp Pro Pro Pro Glu Leu
1               5
```